US008883493B2

(12) United States Patent
Lowenstein et al.

(10) Patent No.: US 8,883,493 B2
(45) Date of Patent: Nov. 11, 2014

(54) ADENOVIRAL VECTOR COMPRISING HERPES SIMPLEX VIRUS TYPE 1 THYMIDINE KINASE AND A TRANSGENE FOR INCREASING THE EXPRESSION OF THE TRANSGENE

(75) Inventors: Pedro R. Lowenstein, Los Angeles, CA (US); Maria Castro, Los Angeles, CA (US)

(73) Assignee: Cedars-Sinai Medical Center, Los Angeles, CA (US)

( * ) Notice: Subject to any disclaimer, the term of this patent is extended or adjusted under 35 U.S.C. 154(b) by 0 days.

(21) Appl. No.: 12/520,500

(22) PCT Filed: Jan. 30, 2008

(86) PCT No.: PCT/US2008/052510
§ 371 (c)(1),
(2), (4) Date: Jun. 19, 2009

(87) PCT Pub. No.: WO2008/095027
PCT Pub. Date: Aug. 7, 2008

(65) Prior Publication Data
US 2010/0143304 A1 Jun. 10, 2010

Related U.S. Application Data

(60) Provisional application No. 60/887,189, filed on Jan. 30, 2007.

(51) Int. Cl.
*C12N 15/63* (2006.01)
*C12N 15/86* (2006.01)
*A61K 48/00* (2006.01)
*C12N 7/00* (2006.01)
*C12N 9/12* (2006.01)

(52) U.S. Cl.
CPC ............ *C12N 15/86* (2013.01); *C12N 2830/00* (2013.01); *C07K 2319/00* (2013.01); *C12N 7/00* (2013.01); *C12N 9/1211* (2013.01); *C12N 2710/10343* (2013.01)
USPC ...... 435/320.1; 435/456; 536/24.1; 514/44 R; 424/199.1

(58) Field of Classification Search
USPC ............ 435/320.1, 456; 536/24.1; 514/44 R; 424/199.1
See application file for complete search history.

(56) References Cited

U.S. PATENT DOCUMENTS

| 5,139,941 A | 8/1992 | Muzyczka et al. |
| 5,173,414 A | 12/1992 | Lebkowski et al. |
| 5,501,979 A | 3/1996 | Geller et al. |
| 5,554,512 A | 9/1996 | Lyman et al. |
| 5,750,398 A | 5/1998 | Johnson et al. |
| 5,824,837 A | 10/1998 | Chen et al. |
| 6,030,956 A | 2/2000 | Boulikas |
| 6,066,624 A | 5/2000 | Woo et al. |
| 6,190,655 B1 | 2/2001 | Lyman et al. |
| 6,291,661 B1 | 9/2001 | Graddis et al. |
| 6,365,394 B1 | 4/2002 | Gao et al. |
| 6,451,593 B1 | 9/2002 | Wittig et al. |
| 6,518,062 B1* | 2/2003 | Blanche et al. ............ 435/320.1 |
| 6,566,128 B1* | 5/2003 | Graham et al. ............... 435/325 |
| 6,630,143 B1 | 10/2003 | Lyman et al. |
| 6,743,631 B1 | 6/2004 | Mason |
| 6,818,439 B1 | 11/2004 | Jolly et al. |
| 6,887,688 B2* | 5/2005 | Lagarias et al. ............. 435/69.7 |
| 7,247,297 B2 | 7/2007 | Weichselbaum et al. |
| 2003/0031681 A1 | 2/2003 | McCart et al. |
| 2004/0009588 A1 | 1/2004 | Chang et al. |
| 2004/0029227 A1 | 2/2004 | Lowenstein et al. |
| 2006/0246038 A1 | 11/2006 | Lowenstein et al. |
| 2008/0181870 A1 | 7/2008 | Lowenstein et al. |
| 2009/0181424 A1* | 7/2009 | Albericio et al. ............ 435/69.1 |

FOREIGN PATENT DOCUMENTS

| AU | 9536584 B2 | 5/1995 |
| EP | 1786474 B1 | 6/2011 |
| EP | 2338524 A1 | 6/2011 |
| GB | 2355460 A | 4/2001 |
| GB | 2397063 A | 7/2004 |
| WO | 92/01070 A1 | 1/1992 |
| WO | 93/03769 A1 | 3/1993 |
| WO | 93/04167 A1 | 3/1993 |
| WO | 95/09654 A1 | 4/1995 |
| WO | 95/09655 A1 | 4/1995 |
| WO | 96/20733 A1 | 7/1996 |
| WO | 00/65078 A1 | 11/2000 |
| WO | 2006/020949 A2 | 2/2006 |
| WO | 2008/095027 A2 | 8/2008 |

OTHER PUBLICATIONS

Blackburn et al. (1999) Int. J. Cancer, vol. 82, 293-297.*
Lee et al. (2002) Cancer Gene Therapy, vol. 9, 267-274.*
Otero et al. (1998) J. Virol., vol. 72(12), 9889-9896.*
Saijo et al. (J. Med. Virol., vol. 58, 387-393.*
Glover et al. (2002) Mol. Ther., vol. 5(5), 509-516.*
Alba et al. (2005) Gene Ther., vol. 12, S18-S27.*
PCT/US08/52510 Publication of PCT Application dated Aug. 7, 2008.
PCT/US08/52510 IPRP dated Aug. 4, 2009.
PCT/US08/52510 Written Opinion dated Aug. 15, 2008.

(Continued)

Primary Examiner — Anne Marie S Wehbe
(74) Attorney, Agent, or Firm — Linda B. Huber; Nixon Peabody LLP

(57) ABSTRACT

Compositions and methods useful in transgene expression are provided. Herpes simplex virus type 1 thymidine kinase sequences ("TK sequences") are used to enhance transgene expression in first generation and high capacity adenoviral vectors. An mCMV promoter-driven β-galactosidase-expressing cassette is combined with TK sequences through direct fusion of the cDNA's. β-galactosidase (transgene) expression is enhanced independent of adenoviral vector selection. Methods of enhancing transgene expression employing the inventive adenoviral vectors are provided, along with pharmaceutical preparations comprising the inventive vectors and kits for enhanced transgene expression.

16 Claims, 9 Drawing Sheets

(56) References Cited

OTHER PUBLICATIONS

King G.D. et al., Flt3L mediated gene therapy in a syngeneic model of glioma with and without pre-existing adenoviral immunity. Database Biosis (Online) Biosciences Information Service. (2005), 19(5): A1406. Abstract.

Check E. Cancer fears cast doubts on future of gene therapy. Nature. (2003), 1421:6.

Southgate, T.D. et al., Long-Term Transgene Expression Within the Anterior Pituitary Gland in Situ: Impact on Circulating Hormone Levels, Cellular and Antibody-Mediated Immune Responses. Endocrinology (2001), 142:464-476.

Zermansky et al., Towards Global and Long-Term Neurological Gene Therapy: Unexpected Transgene Dependent, High-Level, and Widespread Distribution of HSV-1 Thymidine Kinase Throughout the CNS. Molecular Therapy. (2001), 4(5):490-498.

Ali et al., Combined Immunostimulation and Conditional Cytotoxic Gene Therapy Provide Long-Term Survival in a Large Glioma Model. Cancer Research (2005), 65(16):7194-7204.

Ali et al., Inflammatory and Anti-Glioma Effects of an Adenovirus Expressing Human Soluble Fms-Like Tryosine Kinase 3 Ligand (hsFlt3L): Treatment with hsFlt3L Inhibits Intracranial Glioma Progression. Molecular Therapy (2004), 10(6):1071-1084.

Castro et al., Current and Future Strategies for the Treatment of Malignant Brain Tumors. Pharmacology & Therapeutics. (2003), 98:71-108.

Chiocca et al., Viral Therapy for Glioblastoma. Cancer Journal (2003), 9(3):167-179.

Cowsill et al., Central Nervous System Toxicity of Two Adenoviral Vectors Encoding Variants of the Herpes Simplx Virus Type 1 Thymidine Kinase: Reduced Cytotoxicity of a Truncated HSV1-TK. Gene Therapy (2000), 7:679-685.

Curtin et al., Fms-Like Tyrosine Kinase 3 Ligand Recruits Plasmacytoid Dendritic Cells to the Brain. The Journal of Immunology (2006), 176:3566-3577.

Dewey et al., Chronic Brain Inflammation and Persistent Herpes Simplex Virus 1 Thymidine Kinase Expression in Survivors of Syngeneic Glioma Treated by a Adenovirus-Medicated Gene Therapy: Implications for Clinica Trials. Nature Medicine (1999), 5(11):1256-1263.

Dong et al., Antitumor Effect of Secreted Flt3L Can Act at Distant Tumor Sites in a Murine Model of Head and Neck Cancer. Cancer Gene Therapy (2003), 10(2):96-104.

Fulci et al., Oncolytic Viruses for the Therapy of Brain Tumors and other Solid Malignancies: A Review. Frontiers in Bioscience. (2003), 8:346-360.

Kawashita et al., FLT3-Ligand Gene Transfer Increases Antitumor Effects of Radio-Inducible Suicide Gene Therapy for Hepatocellular Carcinoma. Proceeding of the Annual Metting for Cancer Research. (2001), 42.

Klatzmann et al., A Phase I/II of Herpes Simplex Virus Type I Thymidine Kinase "Suicide" Gene Therapy for Recurrent Glioblastoma. Study Group on Gene Therapy for Glioblastoma. Human Gene Therapy (1998), 9(17): 2595-2604.

Lang et al., Phase I Trial of Adenovirus-Mediated p53 Gene Therapy for Recurrent Glioma: Biological and Clinical Results. Journal of Clinical Oncology (2003), 21(13):2508-2518.

Lowenstein., Immunology of Viral-Vector-Mediated Gene Transfer Into the Brain: An Evolutionary and Developmental Perspective. Trends in Immunology. (2002), 23(1):23-30.

Marked et al., Conditionally Replicating Herpes Simplex Virus Mutant, G207 for the Treatment of Malignant Glioma: Results of a Phase I Trial, Gene Therapy. (2000). 7:867-874.

Rainov, N.G., A Phase III Clinical Evaluation of Herpes Simplex Virus Type I Thymidine Kinase and Ganciclovir Gene Therapy as an Adjuvent to Surgical Resection and Radiation in Adults with Previously Untreated Glioblastoma Multiforme. Human Gene Therapy. (2000), 11(17):2389-2401.

Rampling et al., Toxicity Evaluation of Replication-Competent Herpes Simplex Virus (ICP 34.5 Null Mutant 1716) in Patients with Recurrent Malignant Glioma. Gene Therapy. (2000), 7(10):859-866.

Sandmair et al., Thymidine Kinase Gene Therapy for Human Malignant Glioma, Using Replication-Deficient Retroviruses or Adenoviruses. Human Gene Therapy. (2000), 11(16):2197-2205.

Thomas et al., Acute Direct Adenoviral Vector Cytotoxicity and Chronic, but not Acute, Inflammatory Responses Correlate with Decreased Vector-Mediated Transgene Expression in the Brain. Molecular Therapy. (2001), 3(1):36-46.

Thomas et al. Progress and Problems with the use of viral vectors for gene therapy. Nature. (2003), 4:346-358.

GB Patent Application No. 0406539.7 Combined Search and Examination Report dated May 6, 2004.

GB Patent Application No. 0025890.5 Search Report dated Nov. 16, 2000.

GB Patent Application No. 0025890.5 Examination Report dated Aug. 29, 2003.

GB Patent Application No. 0025890.5 Examination Report dated Apr. 16, 2004.

U.S. Appl. No. 09/693,970 Office Action dated Sep. 25, 2002.
U.S. Appl. No. 09/693,970 Office Action dated Jun. 12, 2002.
U.S. Appl. No. 10/395,287 Restriction Requirement dated Apr. 27, 2006.
U.S. Appl. No. 10/395,287 Final Office Action dated Aug. 14, 2006.
U.S. Appl. No. 11/572,391 Office Action dated Feb. 19, 2009.
U.S. Appl. No. 11/572,391 Office Action dated Oct. 13, 2009.
U.S. Appl. No. 11/572,391 Office Action dated Apr. 29, 2010.
EP Application 05804343.1 Search Report dated Oct. 22, 2008.
EP Application 05804343.1 Examination Report dated Feb. 2, 2009.
EP Application 05804343.1 Examination Report dated Jun. 29, 2010.
PCT/US05/28906 Written Opinion dated Jun. 13, 2006.
PCT/US05/28906 International Search Report Jun. 13, 2006.
PCT/US05/28906 IPRP dated Feb. 13, 2007.

Tyynela, K. et al. Adenovirus mediated herpes simplex virus thymidine kinase therapy in BT4C glioma mode. Cancer Gene Therapy. (2002), 9:917-924.

Fecci, P.E. et al., Viruses in the treatment of brain tumors. Neuroimaging Clin N. Am. (2002), 12(4):553-570.

Galanis E. et al., Use of viral fusogenic membrane glycoproteins as novel therapeutic transgenes in gliomas. Human Gene Therapy. (2001), 12(7):811-821.

Dobrovolsky V.N. et al., Pms2 deficiency results in increased mutation in the Hprt gene but not the Tk gene of Tk(+/−) transgenic mice. Mutagenesis. (2003), 18(4): 365-370.

Kahle et al., The Emerging utility of animal models of chronic neurodegenerative disease. Emerging Therapeutic Targets. (2001), 5(1):125-132.

EP 11153885.6 Extended Search Report dated May 27, 2011.

Kawashita Y. et al., A novel therapeutic strategy for hepatocellular carcinoma: Immunomodulation by Flt3-ligand (Flt3L) following whole liver irradiation and radio-inducible HSV-TK gene therapy. International Journal of Radiation Oncology Biology Physics. (2001), 51(2) 105-106. Abstract.

Lazic and Barker. Cell-based therapies for disorders of the CNS. Expert Opin. Ther. Patents. (2005), 15(10):1361-1370.

Verman and Somia. Gene Therapy—promises, problems and prospects. Nature. (1997). 389:239-242.

Santodonato et al. Local and systemic antitumor response after combined therapy of mouse metastatic tumors with tumor cells expressing IFN-a and HSVtk: perspectives for the generation of cancer vaccines. Gene Therapy. (1997), 4:1246-1255.

Russell. Replicating Vectors for Gene Therapy of Cancer: Risks, Limitations and Prospects. European Journal of Cancer. (1994), 30A(8):1165-1171.

Wang Z. et al., In Vivo and in Vitro Glioma Cell Killing Induced by an Adenovirus Expressing Both Cytosine Deaminase and Thymidine Kinase and its Association with Interferon-a. Journal of Neuropathology and Experimental Neurology (1999), 58(8):847-858.

Felzmann, T. et al. Characterization of the antitumor immune response generated by treatment of murine tumors with recombinant adenoviruses expressing HSVtk, IL-2, IL-6 or B7-1. Gene Therapy. (1997), 4:1322-1329.

(56) References Cited

OTHER PUBLICATIONS

O'Malley B.W. et al. The Role of Interleukin-2 in Combination Adenovirus Gene Therapy for Head and Neck Cancer. Molecular Endocrinology. (1997),11(6):667-673.

Gansbacher et al., Interleukin 2 Gene Transfer into Tumor Cells Abrogates Tumorigenicity and Induces Protective Immunity. Journal of Experimental Medicine. (1990), 172:1217-1224.

Minasi et al., The Selective Ablation of Interleukin 2-producing Cells Isolated from Transgenic Mice. Journal of Experimental Medicine. (1993), 177:1451-1459.

Borrelli et al., Targeting of an Inducible Toxic Phenotype in Animal Cells. Proc. Nat'l Acad. Sci. USA (1988). 85:7572-7576.

Golumbek et al., Treatment of Established Renal Cancer by Tumor Cells Engineered to Secrete Interleukin-4. Science. (1991), 254(1):713-716.

U.S. Appl. No. 11/444,050 Non-Final Office Action dated Jun. 26, 2008.

U.S. Appl. No. 11/444,050 Final Office Action dated Apr. 15, 2009.

U.S. Appl. No. 11/444,050 Non-Final Office Action dated Feb. 5, 2010.

U.S. Appl. No. 11/444,050 Final Office Action dated Oct. 15, 2010.

PCT/US08/52510 International Search Report dated Aug. 15, 2008.

U.S. Appl. No. 11/572,391 Non-Final Office Action dated May 22, 2012.

Fulci, G. & Chiocca, A.E. The status of gene therapy for brain tumors. Expert Opin Biol Ther. (2007). 7(2):197. doi: 10.1517/14712598.7.2.197. pp. 1-18.

Stone, D. et al. Viral vectors for gene delivery and gene therapy within the endocrine system. Journal of Endocrinology. (2004). 164: pp. 103-118.

U.S. Appl. No. 11/444,050 Non-Final Office Action dated Feb. 3, 2012.

EP Application No. 11153885.6 Examination Report dated Apr. 11, 2012.

U.S. Appl. No. 11/444,050 Notice of Allowance dated Feb. 28, 2013.

U.S. Appl. No. 11/572,391 Notice of Allowance dated Dec. 18, 2012.

* cited by examiner

Figure 4
A
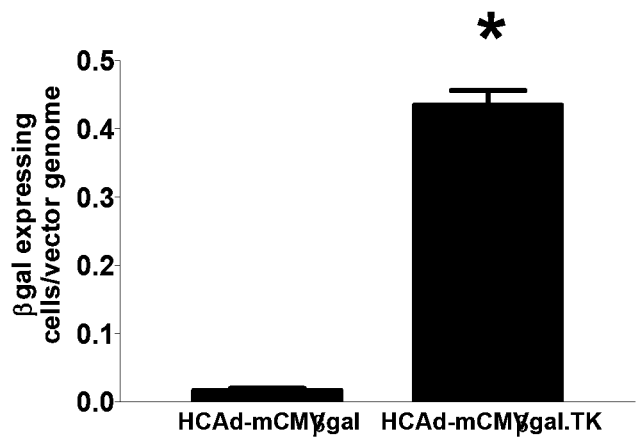
B
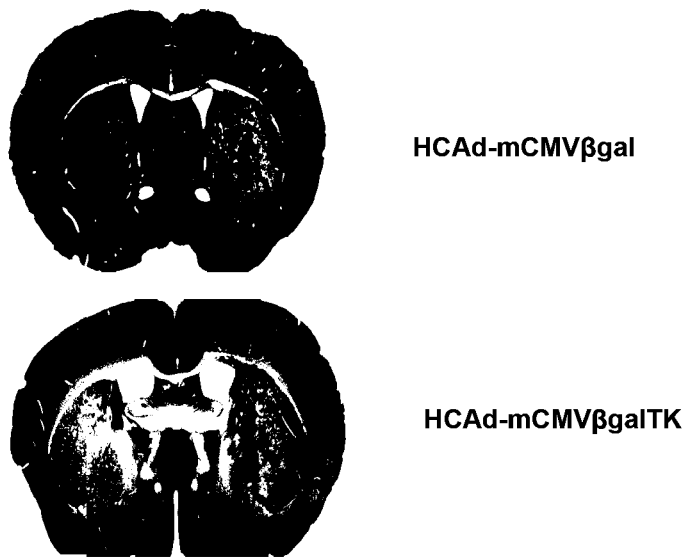
HCAd-mCMVβgal
HCAd-mCMVβgalTK

Figure 5
A
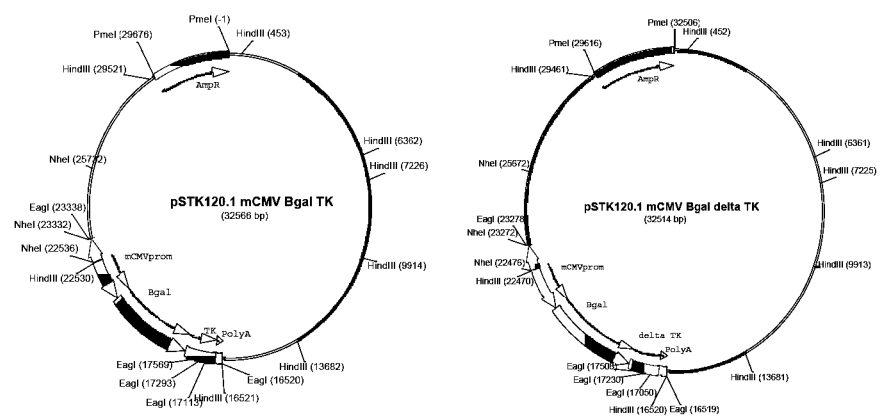
B
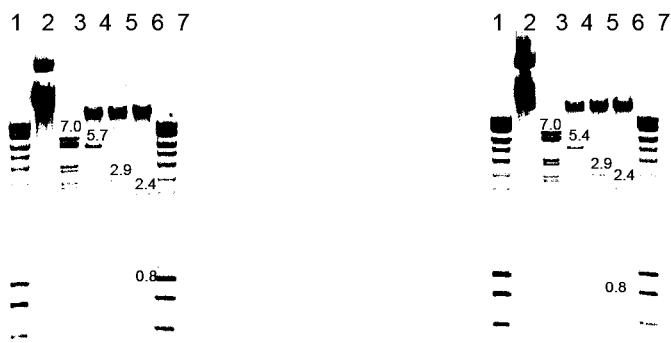

C.

Figure 6
A
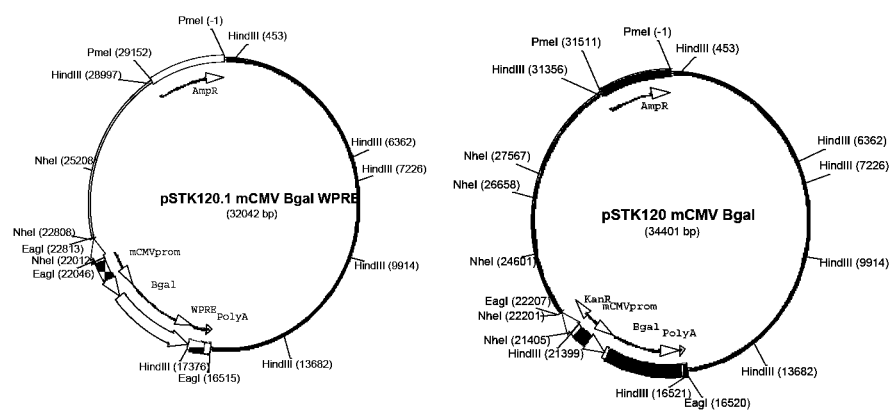
B
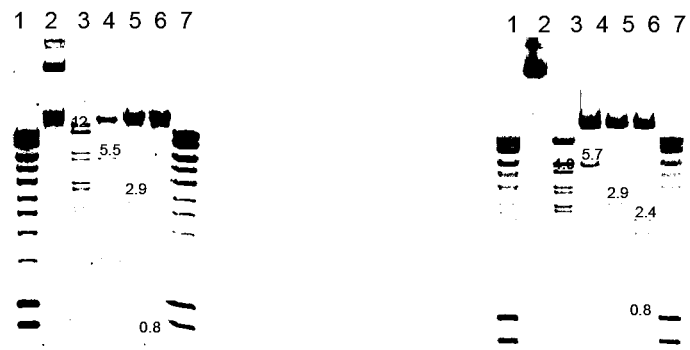

C.

SEQUENCE LISTING

```
<160> NUMBER OF SEQ ID NOS: 3

<210> SEQ ID NO 1
<211> LENGTH: 1131
<212> TYPE: DNA
<213> ORGANISM: Herpes Simplex Virus Type 1

<400> SEQUENCE: 1
atggcttcgt acccggcca ttagcacgcg tctgcgttcg accaggctgc gcgttctcgc      60
ggccatagca accgacgtac ggcgttgcgc cctcgccggc agcaagaagc cacggaagtc     120
cgcccggagc agaaaatgcc cacgctactg cgggtttata tagacggtcc ccacgggatg     180
gggaaaacca ccaccacgca actgctggtg gccctgggtt cgcgcgacga tatcgtctac     240
gtacccgagc cgatgactta ctggcgggtg ctgggggctt ccgagacaat cgcgaacatc     300
tacaccacac aacaccgcct cgaccagggt gagatatcgg ccggggacgc ggcggtggta     360
atgacaagcg cccagataac aatgggcatg ccttatgccg tgaccgacgc cgttctggct     420
cctcatatcg gggggaggc tgggagctca catgccccgc cccggccct caccctcatc      480 ttcgaccgcc atcccatcgc cgccctcctg tgctaccgg ccgcgcgata ccttatgggc      540
agcatgaccc cccaggccgt gctggcgttc gtggccctca tcccgccgac cttgcccggc     600
acaaacatcg tgttgggggc ccttccggag gacagacaca tcgaccgcct ggccaaacgc     660
cagcgccccg gcgagcggct tgacctggct atgctggccg cgattcgccg cgtttacggg     720
ctgcttgcca atacggtgcg gtatctgcag ggcggcgggt cgtggcggga ggattgggga     780
cagctttcgg ggacggccgt gccgcccag ggtgccgagc ccagagcaa cgcgggccca      840 cgaccccaca tcggggacac gttatttacc ctgtttcggg ccccgagtt gctggccccc     900 aacggcgacc tgtataacgt gtttgcctgg gccttggacg tcttggccaa acgcctccgt     960
```

```
cccatgcacg tctttatcct ggattacgac caatcgcccg ccggctgccg ggacgccctg    1020
ctgcaactta cctccgggat ggtccagacc cacgtcacca ccccaggctc cataccgacg    1080
atctgcgacc tggcgcgcac gtttgcccgg gagatggggg aggctaactg a             1131

<210> SEQ ID NO 2
<211> LENGTH: 21
<212> TYPE: DNA
<213> ORGANISM: Artificial Sequence
<220> FEATURE:
<223> OTHER INFORMATION: Forward PCR Primer

<400> SEQUENCE: 2
tccttcagat cttcagttag c                                              21

<210> SEQ ID NO 3
<211> LENGTH: 21
<212> TYPE: DNA
<213> ORGANISM: Artificial Sequence
<220> FEATURE:
<223> OTHER INFORMATION: Reverse PCR Primer

<400> SEQUENCE: 3
cgttctagat ctcataacaa c                                              21
```

ADENOVIRAL VECTOR COMPRISING HERPES SIMPLEX VIRUS TYPE 1 THYMIDINE KINASE AND A TRANSGENE FOR INCREASING THE EXPRESSION OF THE TRANSGENE

This application is the National Phase of International Application PCT/US08/52510, filed Jan. 30, 2008, which designated the U.S. and that International Application was published under PCT Article 21(2) in English. This application also includes a claim of priority under 35 U.S.C. §119(e) to U.S. provisional patent application No. 60/887,189, filed Jan. 30, 2007.

STATEMENT REGARDING FEDERALLY-SPONSORED RESEARCH

The U.S. Government has a paid-up license in this invention and the right in limited circumstances to require the patent owner to license others on reasonable terms as provider for by the terms of Grant No. R01NS42893 awarded by National Insitutes of Health.

FIELD OF THE INVENTION

The invention relates to compositions and methods useful in transgene expression. In particular, the invention relates to the use of herpes simplex virus type 1 thymidine kinase sequences ("TK sequences") to enhance transgene expression in an adenoviral vector.

BACKGROUND OF THE INVENTION

All publications herein are incorporated by reference to the same extent as if each individual publication or patent application was specifically and individually indicated to be incorporated by reference. The following description includes information that may be useful in understanding the present invention. It is not an admission that any of the information provided herein is prior art or relevant to the presently claimed invention, or that any publication specifically or implicitly referenced is prior art.

Adenovirus derived recombinant vectors are attractive tools for gene transfer, including gene transfer into the central nervous system. First generation vectors (Ad) and high-capacity helper-dependent adenoviral vectors (HC-Ad) are the two main different types of vectors derived from adenovirus. Ad vectors are devoid of the essential E1a/1b genes, and are thus routinely grown in cell lines that express these genes in trans to allow adenoviral replication and packaging. HC-Ad genomes retain only cis-acting adenoviral sequences necessary to replicate the viral vector genomes (i.e., the inverted terminal repeats [ITRs] and the packaging signal sequence [ψ]). The absence of wild-type adenoviral sequences from HC-Ad genomes results in lower immunogenicity in vivo and promotes safer, efficient gene transfer with long lasting transgene expression. HC-Ads are grown with a helper virus that provides all essential adenoviral functions for replication in trans. The packaging sequence of the helper virus is flanked by either FRT (flippase [FLP] recombinase target sites) or loxP (Cre recombination targets sites), and thus HC-Ad are growing in either in 293-Flpe or 293-Cre cells. As the genomes replicate, the helper viral genome undergoes recombination that deletes the packaging site ψ; as a consequence, the helper virus genome is less efficiently packaged than the HC-Ad genome.

In spite of the early region gene deletions, and consequent lack of viral replication, first generation Ad vectors have residual expression of viral genes. This leads to a host adaptive immune response. Delivery of Ad vectors results in anti-capsid neutralizing antibodies that block re-infection with the same serotype of Ad vector. Also, injection with Ad vectors induces a CTL response directed against adenoviral proteins and the transgene.

Following systemic delivery of the vector, Ad capsid proteins activate chemokine expression from infected cells. The activation of innate responses by transcription-defective adenovirus particles has been demonstrated in mouse and nonhuman primate models. Serum IL-6, TNFalpha, IL-12 levels and liver toxicity occurred within hours in a dose dependent manner and were induced equally in animals receiving transcription competent or defective Ad vectors. Following intravenous administration, Ad vectors induce a biphasic course of cytokine and chemokine gene expression. The innate host defense system serves to rapidly eliminate Ad vectors, reducing transduction efficiency in vivo. Furthermore, at high titers, adenovirus vectors are associated with acute inflammation that may result in significant morbidity in transduced hosts. In the absence of viral transcription, it has been shown that the effects of the adenovirus particle do not extend beyond 24 hr.

After administration of Adenovirus-derived vectors in the Central Nervous System (CNS) transgene expression persists for long periods of time (i.e., 12 months). Injection of $1 \times 10^6$ to $1 \times 10^7$ iu of either first-generation or high capacity Ad into the brain cause a self-limiting and innate inflammatory reaction characterized by infiltration of macrophages and lymphocytes, increased expression of MHC class I, activation of local microglia and astrocytes localized to the injection site, and an increase in the expression of cytokine and chemokine genes (Byrnes et al. (1995). Adenovirus gene transfer causes inflammation in the brain. Neuroscience, 66(4):1015-24; Lowenstein (2000). Un pour tous, tous pour un. Trends Neurosci. 23(10):467-8; Zirger et al. (2006). Rapid upregulation of interferon-regulated and chemokine mRNAs upon injection of 108 international units, but not lower doses, of adenoviral vectors into the brain. J Virol. 80:5655-9.). Importantly, this initial innate inflammatory response is transient and does not reduce long term vector expression. However, acute adenovirus induced cytotoxicity is seen when vector doses of $\geq 10^8$ iu are used to transduce the brain. These early innate inflammatory immune responses are caused by Ad vectors, but also by HC-Ad, or ultraviolet (UV)/psoralen-inactivated Ad; this confirms that viral genes are not necessary to stimulate innate immune responses; nevertheless, continued expression of viral antigens may be needed to stimulate an adaptive immune response against adenovirus, with an increase in neutralizing antibody titers and anti-Ad T cells. Furthermore, Barcia et al. showed novel helper-dependent high-capacity Ad sustain transgene expression for up to one year, even when injected into the brains of animals immunized against adenovirus preceding brain gene transfer. This strongly supports the use of HC-Ad for gene transfer into the brain, not only for short term gene expression, but also for long term gene expression, and potentially for gene therapy for human neurological diseases. Further, the incapacity of HC-Ad to induce systemic antiadenoviral immune responses further supports the safety and potential efficacy of these vectors (Barcia et al. (2007). Sustained, one year expression from high-capacity helper-dependent adenoviral vectors delivered to the brain of animals with a pre-existing systemic anti-adenoviral immune response: implications for clinical trails. In press).

While injection of first generation Ad vectors into the brain parenchyma causes acute cellular- and cytokine-mediated inflammatory responses, this does not affect transgene expression and it is dose dependent. In the presence of adenoviral immune responses, transgene expression from first generation adenovirus is rapidly ablated. Adenovirus induced cytotoxicity is only seen when high vector doses of greater than $10^8$ i.u. are used to transduce the target tissue.

An important issue in gene therapy is how to improve the overall efficiency of gene delivery. Increasing transgene expression per vector genome delivered is one method for achieving this aim. An approach to do so is through the use of sequences that either increase the number of transcript copies, or reduce the turnover of the mRNA; both approaches would achieve higher level of protein being expressed per vector particle. Recently, the woodchuck hepatitis virus post-transcriptional regulatory element (WPRE) has been utilized in gene transfer vectors to enhance transgene expression. Enhanced transgene expression in adenovirus vectors, adeno-associated virus vectors, lentivirus vectors and MLV-derived vectors harboring WPRE has been reported (Loeb et al. (1999). Enhanced expression of transgenes from adeno-associated virus vectors with the woodchuck hepatitis virus post-transcriptional regulatory element: implications for gene therapy. Hum Gene Ther. 10:2295-305; Zufferey et al. (1999). Woodchuck hepatitis virus posttranscriptional regulatory element enhances expression of transgenes delivered by retroviral vectors. J Virol. 73:2886-92; Glover et al. (2002). Adenoviral-mediated, high-level, cell-specific transgene expression: a SYN1-WPRE cassette mediates increased transgene expression with no loss of neuron specificity. Mol Ther 5:509-16; Ketteler et al. (2002). Enhanced transgene expression in primitive hematopoietic progenitor cells and embryonic stem cells efficiently transduced by optimized retroviral hybrid vectors. Gene Ther. 9:477-87; Mautino et al. (2002). Enhanced inhibition of human immunodeficiency virus type 1 replication by novel lentiviral vectors expressing human immunodeficiency virus type 1 envelope antisense RNA. Hum Gene Ther. 13:1027-37; Xu et al. (2003). Woodchuck hepatitis virus post-transcriptional regulation element enhances transgene expression from adenovirus vectors. Biochim Biophys Acta. 1621:266-71).

The inventors have previously demonstrated long term expression of Herpes virus type 1 Thymidine kinase (HSV1-TK) in experiments in which Ad-expressing HSV1-TK had been used in a paradigm of gene therapy for the treatment of rat glioblastoma. The inventors found high level, anatomically widespread and long term expression of HSV-1-TK (Dewey et al. (1999). Chronic brain inflammation and persistent herpes simplex virus 1 thymidine kinase expression in survivors of syngeneic glioma treated by adenovirus-mediated gene therapy: implications for clinical trials. Nat Med. 5:1256-63). If a second transgene was encoded by a second vector, co-injected with Ad-TK, no changes were seen in the expression of β-galactosidase, suggesting the hypothesis that the observed effects were to HSV1-TK (Zermansky et al. (2001). Towards global and long-term neurological gene therapy: unexpected transgene dependent, high-level, and widespread distribution of HSV-1 thymidine kinase throughout the CNS, Mol Ther. 4(5): 490-8).

However, it was recently shown that HSV1-TK sequences could restitute expression to genes that had been made intronless, where the expression is strictly intron-dependent. HSV1-TK sequences fused to the 5' end of a highly intron-dependent β-globin (Liu et al. (1995). HnRNP L binds a cis-acting RNA sequence element that enables intron-dependent gene expression. Genes Dev. 9:1766-80; Otero et al. (1998). Splicing-independent expression of the herpes simplex virus type 1 thymidine kinase gene is mediated by three cis-acting RNA subelements. J Virol. 72:9889-96), or fused to the 3' end of the Hepatitis virus B surface antigen gene has been shown to provide expression in a intron-independent manner.

High doses of adenoviral vectors delivered to the brain have been demonstrated to induce adaptive immune responses that mediate detrimental side effects in clinical models. Enhancement of transgene expression constitutes an important shortcoming in an Ad-based therapy.

In light of the value of recombinant vectors for gene transfer and delivery and the deficiency of the overall efficiency of gene delivery, there exists a need in the art for improvements in the overall efficiency of gene delivery.

BRIEF DESCRIPTION OF THE FIGURES

Exemplary embodiments are illustrated in referenced figures. It is intended that the embodiments and figures disclosed herein are to be considered illustrative rather than restrictive.

FIG. 4 depicts in vivo transgene expression from HCAd-mCMV.βgal and HCAd-mCMV.βgal.TK within the mouse brain in accordance with various embodiments of the present invention. Mice were injected with $5.0 \times 10^4$ blue forming units (BFU) of HCAd-mCMV.βgal or HCAd-mCMV.β-gal.TK. After 7 days, transgene expression was determined by β-galactosidase immunocytochemistry. (A) βgal expressing cells per inoculated vector genome in mouse striatum. βgal expressing cells were quantified using the Stereo Investigator software as described herein. Bonferroni analysis after One way ANOVA *, P<0.05 versus control group (infected cells with the corresponding vector bearing mCMV.βgal cassette). (B) Images show βimmunopositive cells in striatal sections. Brain sections were stained for βgal-specific detection: HCAd-mCMV.βgal (top panel) and HCAd-mCMV.β-gal.TK (bottom panel).

DESCRIPTION OF THE INVENTION

Figure 1:
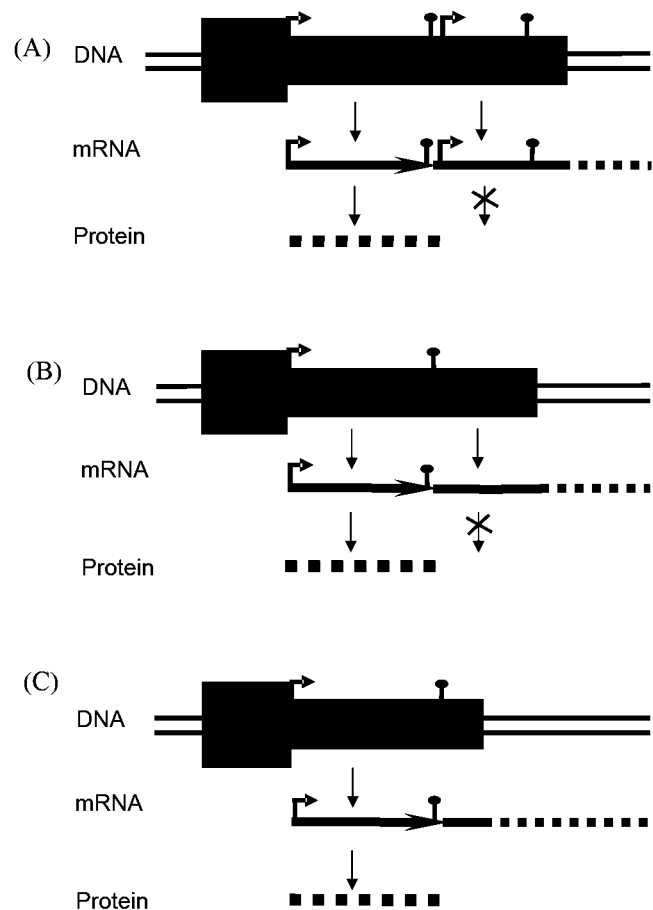
FIG. 1 depicts post-transcriptional regulatory elements in accordance with various embodiments of the present invention. (A) HVS1-Thymidine kinase was fused to βgalactosidase sequence. (B) Woodchuck postranscriptional regulatory element was fused to the βgalactosidase gene. (C) Control, no postranscriptional regulatory element present in the construct. The posttranscriptional regulatory sequence is transcribed with the transgene sequence in a unique mRNA. Only the transgene sequence is translated into an amino acid sequence.

All references cited herein are incorporated by reference in their entirety as though fully set forth. Unless defined otherwise, technical and scientific terms used herein have the same meaning as commonly understood by one of ordinary skill in the art to which this invention belongs. Singleton et al., *Dictionary of Microbiology and Molecular Biology* 3rd ed., J. Wiley & Sons (New York, N.Y. 2001); March, *Advanced Organic Chemistry Reactions, Mechanisms and Structure* 5th ed., J. Wiley & Sons (New York, N.Y. 2001); and Sambrook and Russel, *Molecular Cloning: A Laboratory Manual* 3rd ed., Cold Spring Harbor Laboratory Press (Cold Spring Harbor, N.Y. 2001), provide one skilled in the art with a general guide to many of the terms used in the present application.

"Gene transfer" or "gene delivery" refers to methods or systems for reliably inserting foreign DNA into host cells. Such methods can result in transient expression of non-integrated transferred DNA, extrachromosomal replication and expression of transferred replicons (e.g., episomes), or integration of transferred genetic material into the genomic DNA of host cells. Gene transfer provides a unique approach for the treatment of acquired and inherited diseases. A number of systems have been developed for gene transfer into mammalian cells. See, e.g., U.S. Pat. No. 5,399,346. Examples of well known vehicles for gene transfer include adenovirus and recombinant adenovirus (RAd), adeno-associated virus (AAV), herpes simplex virus type 1 (HSV-1), and lentivirus (LV).

"Mammal" as used herein refers to any member of the class Mammalia, including, without limitation, humans and non-human primates such as chimpanzees and other apes and monkey species; farm animals such as cattle, sheep, pigs, goats and horses; domestic mammals such as dogs and cats; laboratory animals including rodents such as mice, rats and guinea pigs, and the like. The term does not denote a particular age or sex. Thus, adult and newborn subjects, as well as fetuses, whether male or female, are intended to be included within the scope of this term.

"Therapeutically effective amount" as used herein refers to that amount which is capable of achieving beneficial results in a patient. A therapeutically effective amount can be determined on an individual basis and will be based, at least in part, on consideration of the physiological characteristics of the mammal, the type of delivery system or therapeutic technique used and the time of administration relative to the progression of the disease.

"Treatment" and "treating," as used herein refer to both therapeutic treatment and prophylactic or preventative measures, wherein the object is to prevent, slow down and/or lessen the disease even if the treatment is ultimately unsuccessful.

"AAV vector" refers to any vector derived from an adeno-associated virus serotype, including, without limitation, AAV-1, AAV-2, AAV-3, AAV-4, AAV-5, AAVX7, etc. AAV vectors can have one or more of the AAV wild-type genes deleted in whole or in part, preferably the Rep and/or Cap genes, but retain functional flanking inverted terminal repeat ("ITR") sequences. Functional ITR sequences are generally necessary for the rescue, replication and packaging of the AAV virion. Thus, an AAV vector is defined herein to include at least those sequences required in cis for replication and packaging (e.g., functional ITRs) of the virus. The ITRs need not be the wild-type nucleotide sequences, and may be altered (e.g., by the insertion, deletion or substitution of nucleotides) so long as the sequences provide for functional rescue, replication and packaging. A number of adenovirus-based gene delivery systems have also been developed. Human adenoviruses are double-stranded DNA viruses which enter cells by receptor-mediated endocytosis. These viruses are particularly well suited for gene transfer because they are easy to grow and manipulate and they exhibit a broad host range both in vivo and in vitro. Adenovirus is easily produced at high titers and is stable so that it can be purified and stored. Even in the replication-competent form, adenoviruses generally cause only low level morbidity and are generally not associated with human malignancies. For descriptions of various adenovirus-based gene delivery systems, see, e.g., Haj-Ahmad and Graham (1986). J. Virol. 57:267-274; Bett et al. (1993). J. Virol. 67:5911-5921; Mittereder et al. (1994). Human Gene Therapy 5:717-729; Seth et al. (1994). J. Virol. 68:933-940; Barr et al. (1994). Gene Therapy 1:51-58; Berkner, K. L. (1988). BioTechniques 6:616-629; and Rich et al. (1993). Human Gene Therapy 4:461-476. The construction of recombinant adeno-associated virus ("rAAV") vectors has also been described. See, e.g., U.S. Pat. Nos. 5,173,414 and 5,139,941; International Patent Publication Numbers WO 92/01070 (published Jan. 23, 1992) and WO 93/03769 (published Mar. 4, 1993); Lebkowski et al. Molec. Cell. Biol. 8:3988-3996 (1988); Vincent et al., Vaccines 90 (Cold Spring Harbor Laboratory Press) (1990); Carter, B. J. Current Opinion in Biotechnology 3:533-539 (1992); Muzyczka, N., Current Topics in Microbiol. and Immunol. 158:97-129 (1992); and Kotin, R. M. Human Gene Therapy 5:793-801 (1994).

"Recombinant virus" refers to a virus that has been genetically altered (e.g., by the addition or insertion of a heterologous nucleic acid construct into the particle).

"AAV virion" refers to a complete virus particle, such as a wild-type ("wt") AAV virus particle (i.e., including a linear, single-stranded AAV nucleic acid genome associated with an AAV capsid protein coat). In this regard, single-stranded AAV nucleic acid molecules of either complementary sense (i.e., "sense" or "antisense" strands) can be packaged into any one AAV virion; both strands are equally infectious.

A "recombinant AAV virion" or "rAAV virion" is defined herein as an infectious, replication-defective virus composed of an AAV protein shell, encapsidating a heterologous DNA molecule of interest (e.g., HSV1-TK) which is flanked on both sides by AAV ITRs. A rAAV virion may be produced in a suitable host cell which has had an AAV vector, AAV helper functions and accessory functions introduced therein. In this manner, the host cell is rendered capable of encoding AAV polypeptides that are required for packaging the AAV vector (i.e., containing a recombinant nucleotide sequence of interest) into recombinant virion particles for subsequent gene delivery.

The term "transfection" is used herein to refer to the uptake of foreign DNA by a cell. A cell has been "transfected" when exogenous DNA has been introduced inside the cell membrane. A number of transfection techniques are generally known in the art. See, e.g., Graham et al. Virology, 52:456 (1973); Sambrook et al. Molecular Cloning, a laboratory manual, Cold Spring Harbor Laboratories, New York (1989); Davis et al., Basic Methods in Molecular Biology, Elsevier (1986), and Chu et al. *Gene* 13:197 (1981). Such techniques can be used to introduce one or more exogenous DNA moieties, such as a plasmid vector and other nucleic acid molecules, into suitable host cells. The term refers to both stable and transient uptake of the genetic material.

The term "transduction" denotes the delivery of a DNA molecule to a recipient cell either in vivo or in vitro, via a replication-defective viral vector, such as via a recombinant AAV virion.

The term "heterologous," as it relates to nucleic acid sequences such as gene sequences and control sequences, denotes sequences that are not normally joined together and/or are not normally associated with a particular cell. Thus, a "heterologous" region of a nucleic acid construct or a vector is a segment of nucleic acid within or attached to another nucleic acid molecule that is not found in association with the other molecule in nature. For example, a heterologous region of a nucleic acid construct could include a coding sequence flanked by sequences not found in association with the coding sequence in nature. Another example of a heterologous coding sequence is a construct where the coding sequence itself is not found in nature (e.g., synthetic sequences having codons different from the native gene). Similarly, a cell transformed with a construct which is not normally present in the cell would be considered heterologous for purposes of this invention. Allelic variation or naturally occurring mutational events do not give rise to heterologous DNA, as used herein.

"DNA" is meant to refer to a polymeric form of deoxyribonucleotides (i.e., adenine, guanine, thymine and cytosine) in double-stranded or single-stranded form, either relaxed or supercoiled. This term refers only to the primary and secondary structure of the molecule, and does not limit it to any particular tertiary forms. Thus, this term includes single- and double-stranded DNA found, inter alia, in linear DNA molecules (e.g., restriction fragments), viruses, plasmids, and chromosomes. In discussing the structure of particular DNA molecules, sequences may be described herein according to the normal convention of giving only the sequence in the 5' to 3' direction along the non-transcribed strand of DNA (i.e., the strand having the sequence homologous to the mRNA). The term captures molecules that include the four bases adenine, guanine, thymine and cytosine, as well as molecules that include base analogues which are known in the art.

A "gene" or "coding sequence" or a sequence which "encodes" a particular protein is a nucleic acid molecule that is transcribed (in the case of DNA) and translated (in the case of mRNA) into a polypeptide in vitro or in vivo when placed under the control of appropriate regulatory sequences. The boundaries of the gene are determined by a start codon at the 5' (i.e., amino) terminus and a translation stop codon at the 3' (i.e., carboxy) terminus. A gene can include, but is not limited to, cDNA from prokaryotic or eukaryotic mRNA, genomic DNA sequences from prokaryotic or eukaryotic DNA, and even synthetic DNA sequences. A transcription termination sequence will usually be located 3' to the gene sequence.

The term "control elements" refers collectively to promoter regions, polyadenylation signals, transcription termination sequences, upstream regulatory domains, origins of replication, internal ribosome entry sites ("IRES"), enhancers, and the like, which collectively provide for the replication, transcription and translation of a coding sequence in a recipient cell. Not all of these control elements need always be present, so long as the selected coding sequence is capable of being replicated, transcribed and translated in an appropriate host cell.

The term "promoter region" is used herein in its ordinary sense to refer to a nucleotide region including a DNA regulatory sequence, wherein the regulatory sequence is derived from a gene which is capable of binding RNA polymerase and initiating transcription of a downstream (3'-direction) coding sequence.

"Operably linked" refers to an arrangement of elements wherein the components so described are configured so as to perform their usual function. Thus, control elements operably linked to a coding sequence are capable of effecting the expression of the coding sequence. The control elements need not be contiguous with the coding sequence, so long as they function to direct the expression thereof. Thus, for example, intervening untranslated yet transcribed sequences can be present between a promoter sequence and the coding sequence and the promoter sequence can still be considered "operably linked" to the coding sequence.

For the purpose of describing the relative position of nucleotide sequences in a particular nucleic acid molecule throughout the instant application, such as when a particular nucleotide sequence is described as being situated "upstream," "downstream," "5'," or "3" relative to another sequence, it is to be understood that it is the position of the sequences in the non-transcribed strand of a DNA molecule that is being referred to as is conventional in the art.

"Isolated" as used herein when referring to a nucleotide sequence, refers to the fact that the indicated molecule is present in the substantial absence of other biological macromolecules of the same type. Thus, an "isolated nucleic acid molecule which encodes a particular polypeptide" refers to a nucleic acid molecule that is substantially free of other nucleic acid molecules that do not encode the subject polypeptide. However, the molecule may include some additional bases or moieties that do not deleteriously affect the basic characteristics of the composition.

In the present invention the inventors evaluated the use of TK sequences to increase the expression of transgenes in both first generation and HC-Ad vectors.

The inventors utilized a mCMV promoter-driven βgal-expressing cassette that was combined with TK-derived sequences through direct fusion of the cDNAs. The inventors found that when TK sequences are fused to the β-galactosidase transgene they significantly enhanced (i.e., increase) transgene expression independent of the type of adenoviral vector tested. WPRE did have a positive effect in first generation Ad vectors, but did not increase transgene expression when encoded in HCAd vectors. The inventors thus describe a novel mechanism to increase transgene expression in viral vectors. Furthermore, the fact that TK worked in conditions in which WPRE did not, supports the idea that TK and WPRE enhance transgene expression through different mechanisms.

Various embodiments of the present invention are based on the inventors' discovery of the ability of TK to significantly enhance transgene expression.

Thus, various embodiments of the present invention provide for an expression vector capable of increasing the expression of a transgene, the expression vector comprising the herpes simplex virus type 1 thymidine kinase (HSV1-TK) and the transgene. In a further embodiment, the expression vector may comprise a mCMV promoter. In one embodiment, the mCMV promoter is operably linked to the transgene and HSV1-TK. In one embodiment, HSV1-TK is fused to the transgene. In one embodiment, HSV1-TK is fused to the 3' end of the transgene. In another embodiment, HSV1-TK is fused to the 5' end of the transgene. In one embodiment, the expression vector may be an adenoviral vector. In another embodiment, the expression vector may be a recombinant vector. In one embodiment, the expression vector may be a first generation adenoviral vector. In another embodiment, the expression vector may be a high-capacity adenoviral vector. In another embodiment, the expression vector of the present invention is suitable for genetic therapy.

Other embodiments of the present invention provide for a method of increasing the expression of a protein encoded by a transgene in a cell, in vivo, comprising providing an expression vector of the present invention that encodes the transgene, introducing the expression vector into a cell in vivo and maintaining the cell in vivo under conditions permitting increased expression of the transgene in the cell.

Additional embodiments of the present invention provide for a method of increasing the expression of a protein encoded by a transgene in a cell, in vitro, comprising providing an expression vector of the present invention that encodes the transgene, introducing the expression vector into a cell in vitro and maintaining the cell in vitro under conditions permitting increased expression of the transgene in the cell.

Additional embodiments of the present invention provide for a method of treating a patient with a disease, comprising introducing into the patient an expression vector of the present invention that encodes a protein that is needed by the patient, such that an increased amount of the protein is expressed and is effective to alleviate a symptom of the disease.

In various embodiments, the expression vectors according to the invention may be formulated for delivery via any route of administration. "Route of administration" may refer to any administration pathway known in the art, including but not limited to aerosol, nasal, oral, transmucosal, transdermal or parenteral. "Parenteral" refers to a route of administration that is generally associated with injection, including intraorbital, infusion, intraarterial, intracapsular, intracardiac, intradermal, intramuscular, intraperitoneal, intrapulmonary, intraspinal, intrasternal, intrathecal, intrauterine, intravenous, subarachnoid, subcapsular, subcutaneous, transmucosal, or transtracheal. Via the parenteral route, the compositions may be in the form of solutions or suspensions for infusion or for injection, or as lyophilized powders. In one embodiment of the present invention the inventive compositions are injected directly into the brain of a mammal.

In additional embodiments, the expression vectors according to the invention may further comprise a pharmaceutically acceptable carrier. "Pharmaceutically acceptable carrier" as used herein refers to a pharmaceutically acceptable material, composition, or vehicle that is involved in carrying or transporting a compound of interest from one tissue, organ, or portion of the body to another tissue, organ, or portion of the body. For example, the carrier may be a liquid or solid filler, diluent, excipient, solvent, or encapsulating material, or a combination thereof. Each component of the carrier must be "pharmaceutically acceptable" in that it must be compatible with the other ingredients of the formulation. It must also be suitable for use in contact with any tissues or organs with which it may come in contact, meaning that it must not carry a risk of toxicity, irritation, allergic response, immunogenicity, or any other complication that excessively outweighs its therapeutic benefits.

The expression vectors according to the invention can also be encapsulated, tableted or prepared in an emulsion or syrup for oral administration. Pharmaceutically acceptable solid or liquid carriers may be added to enhance or stabilize the composition, or to facilitate preparation of the composition. Liquid carriers include syrup, peanut oil, olive oil, glycerin, saline, alcohols and water. Solid carriers include starch, lactose, calcium sulfate, dihydrate, terra alba, magnesium stearate or stearic acid, talc, pectin, acacia, agar or gelatin. The carrier may also include a sustained release material such as glyceryl monostearate or glyceryl distearate, alone or with a wax.

The pharmaceutical preparations are made following the conventional techniques of pharmacy involving milling, mixing, granulation, and compressing, when necessary, for tablet forms; or milling, mixing and filling for hard gelatin capsule forms. When a liquid carrier is used, the preparation will be in the form of a syrup, elixir, emulsion or an aqueous or non-aqueous suspension. Such a liquid formulation may be administered directly p.o. or filled into a soft gelatin capsule.

The expression vectors according to the invention may be delivered in a therapeutically effective amount. The precise therapeutically effective amount is that amount of the composition that will yield the most effective results in terms of efficacy of treatment in a given subject. This amount will vary depending upon a variety of factors, including but not limited to the characteristics of the therapeutic compound (including activity, pharmacokinetics, pharmacodynamics, and bioavailability), the physiological condition of the subject (including age, sex, disease type and stage, general physical condition, responsiveness to a given dosage, and type of medication), the nature of the pharmaceutically acceptable carrier or carriers in the formulation, and the route of administration. One skilled in the clinical and pharmacological arts will be able to determine a therapeutically effective amount through routine experimentation, for instance, by monitoring a subject's response to administration of a compound and adjusting the dosage accordingly. For additional guidance, see *Remington: The Science and Practice of Pharmacy* (Gennaro ed. 20th edition, Williams & Wilkins Pa., USA) (2000). In one embodiment, a therapeutically effective amount of the expression vectors of the present invention may be an amount that is less than amounts administered in the prior art. This may be attributed to the increased expression of the transgene which may require a smaller amount of the expression vector to be therapeutically effective.

The present invention is also directed to a kit for in vivo or in vitro enhanced expression of the transgene. The kit is useful for practicing the inventive methods. The kit is an assemblage of materials or components, including at least one of the inventive expression vectors comprising the transgene. Thus, in some embodiments the kit contains compositions including viral vectors expressing TK and the transgene.

The exact nature of the components configured in the inventive kit depends on its intended purpose. For example, some embodiments of the kit are configured for the purpose of in vivo or in vitro expression in mammalian cells. Other embodiments are configured for the purpose of treating mammalian cells in vivo (i.e., for treating mammalian subjects in need of treatment, for example, subjects with cancer). In one embodiment, the kit is configured particularly for the purpose of in vivo expression or in human cells. In another embodiment, the kit is configured particularly for the purpose of treating human subjects.

Instructions for use may be included in the kit. "Instructions for use" typically include a tangible expression describing the technique to be employed in using the components of the kit to effect a desired outcome, such as the in vitro or in vivo enhanced expression of the transgene in cells. Optionally, the kit also contains other useful components, such as, diluents, buffers, pharmaceutically acceptable carriers, specimen containers, syringes, stents, catheters, pipetting or measuring tools, or other useful paraphernalia as will be readily recognized by those of skill in the art.

The materials or components assembled in the kit can be provided to the practitioner stored in any convenient and suitable ways that preserve their operability and utility. For example the components can be in dissolved, dehydrated, or lyophilized form; they can be provided at room, refrigerated or frozen temperatures. The components are typically contained in suitable packaging material(s). As employed herein, the phrase "packaging material" refers to one or more physical structures used to house the contents of the kit, such as inventive compositions and the like. The packaging material is constructed by well known methods, preferably to provide a sterile, contaminant-free environment. The packaging materials employed in the kit are those customarily utilized in polynucleotide-based or peptide-based systems. As used herein, the term "package" refers to a suitable solid matrix or material such as glass, plastic, paper, foil, and the like, capable of holding the individual kit components. Thus, for example, a package can be a glass vial used to contain suitable quantities of an inventive composition containing nucleic acid components. The packaging material generally has an external label which indicates the contents and/or purpose of the kit and/or its components.

One of skill in the art will realize that the expression of any number of transgenes may be enhanced through the use of the expression vectors, methods of enhancing expression, pharmaceutical compositions, and kits of the various embodiments of the present invention. Accordingly, one of skill in the art will be able to select appropriate transgenes to use in the inventive expression vectors according to the particular problem being addressed. Solely by way of example, one of skill in the art may select a transgene for which increased expression may be useful in treating a particular human or animal disease or condition.

Increased transgene expression per viral vector genome is an important goal in vector development for gene therapy. Herein the inventors demonstrate that the herpes simplex virus thymidine kinase (HSV1-TK) gene (1131 bp) (SEQ ID NO.1) fused to the 3' end of β-galactosidase increases transgene expression from both first generation adenovirus vectors (Ad) [2.5-10 fold], and from high capacity (HCAd) vectors [2-18-fold] in murine, dog, primate and human cell lines. In vivo expression from HCAd was increased 25 fold. Thus, HSV1-TK can be used to increase transgene expression per viral vector genome to reduce dose, and increase safety and efficacy of clinical gene therapy vectors.

Adenovirus vectors are effective vectors for gene transfer and gene therapy. However, they can induce dose-dependent innate and adaptive immune responses (Liu et al. (2003). The role of capsid-endothelial interactions in the innate immune response to adenovirus vectors. Hum Gene Ther 14:627-43; Muruve, D. A. (2004). The innate immune response to adenovirus vectors. Hum Gene Ther 15:1157-66; Muruve et al. (1999). Adenoviral gene therapy leads to rapid induction of multiple chemokines and acute neutrophil-dependent hepatic injury in vivo. Hum Gene Ther 10:965-76; Schnell et al. (2001). Activation of innate immunity in nonhuman primates following intraportal administration of adenoviral vectors. Mol Ther 3:708-22; Worgall et al. (1997). Innate immune mechanisms dominate elimination of adenoviral vectors following in vivo administration. Hum Gene Ther 8:37-44; Zhang et al. (2001). Acute cytokine response to systemic adenoviral vectors in mice is mediated by dendritic cells and macrophages. Mol Ther 3:697-707; Zirger et al. (2006). Rapid upregulation of interferon-regulated and chemokine mRNAs upon injection of 108 international units, but not lower doses, of adenoviral vectors into the brain. J Virol 80:5655-9). Thus, lowering the total dose of viral vector needed will result in safer, more effective gene therapy, and longer term gene transfer. An increase in transgene expression per vector genome would achieve this aim. An approach to do so is through the use of sequences that either increase the number of transcript copies (e.g., stronger promoters), or reduce the turnover of the mRNA (e.g., the woodchuck hepatitis virus post-transcriptional regulatory element [WPRE]) (Appleby et al. (2003). A novel combination of promoter and enhancers increases transgene expression in vascular smooth muscle cells in vitro and coronary arteries in vivo after adenovirus-mediated gene transfer. Gene Ther 10:1616-22; Glover et al. (2002). Adenoviral-mediated, high-level, cell-specific transgene expression: a SYN1-WPRE cassette mediates increased transgene expression with no loss of neuron specificity. Mol Ther 5:509-16; Johansen et al. (2003). Increased in vitro and in vivo transgene expression levels mediated through cis-acting elements. J Gene Med 5:1080-9; Ketteler et al. (2002). Enhanced transgene expression in primitive hematopoietic progenitor cells and embryonic stem cells efficiently transduced by optimized retroviral hybrid vectors. Gene Ther 9:477-87; Loeb et al. (1999). Enhanced expression of transgenes from adeno-associated virus vectors with the woodchuck hepatitis virus posttranscriptional regulatory element: implications for gene therapy. Hum Gene Ther 10:2295-305; Mautino et al. (2002). Enhanced inhibition of human immunodeficiency virus type 1 replication by novel lentiviral vectors expressing human immunodeficiency virus type 1 envelope antisense RNA. Hum Gene Ther 13:1027-37; Mian et al. (2004). Long-term correction of ornithine transcarbamylase deficiency by WPRE-mediated overexpression using a helper-dependent adenovirus. Mol Ther 10:492-9; Moreau-Gaudry et al. (2001). High-level erythroid-specific gene expression in primary human and murine hematopoietic cells with self-inactivating lentiviral vectors. Blood 98:2664-72; Ramezani et al. (2000). Lentiviral vectors for enhanced gene expression in human hematopoietic cells. Mol Ther 2:458-69; Xu et al. (2003). Woodchuck hepatitis virus post-transcriptional regulation element enhances transgene expression from adenovirus vectors. Biochim Biophys Acta 1621:266-71; Zufferey et al. (1999). Woodchuck hepatitis virus posttranscriptional regulatory element enhances expression of transgenes delivered by retroviral vectors. J Virol 73:2886-92). Recently, the inventors noticed high levels of expression of herpes simplex virus type 1 thymidine kinase (HSV1-TK) encoded by a first generation adenoviral vector (Dewey et al. (1999). Chronic brain inflammation and persistent herpes simplex virus 1 thymidine kinase expression in survivors of syngeneic glioma treated by adenovirus-mediated gene therapy: implications for clinical trials. Nat Med 5:1256-63). At the same time it had been shown that HSV1-TK sequences restitute expression to genes that had been made intronless (Liu et al. (1995). HnRNP L binds a cis-acting RNA sequence element that enables intron-dependent gene expression. Genes Dev 9:1766-80; Otero et al. (1998). Splicing-independent expression of the herpes simplex virus type 1 thymidine kinase gene is mediated by three cis-acting RNA subelements. J Virol 72:9889-96). HSV1-TK sequences fused to the 5' end of a highly intron-dependent mammalian gene, i.e., β-globin (Otero et al. (1998). Splicing-independent expression of the herpes simplex virus type 1 thymidine kinase gene is mediated by three cis-acting RNA subelements. J Virol 72:9889-96), or fused to the 3' end of the hepatitis B virus surface antigen gene (Otero et al. (1998). Splicing-independent expression of the herpes simplex virus type 1 thymidine kinase gene is mediated by three cis-acting RNA subelements. J Virol 72:9889-96) provided expression in an intron-independent manner. So far, the use of HSV1-TK elements in viral vectors to increase transgene expression has not been investigated.

Figure 2:
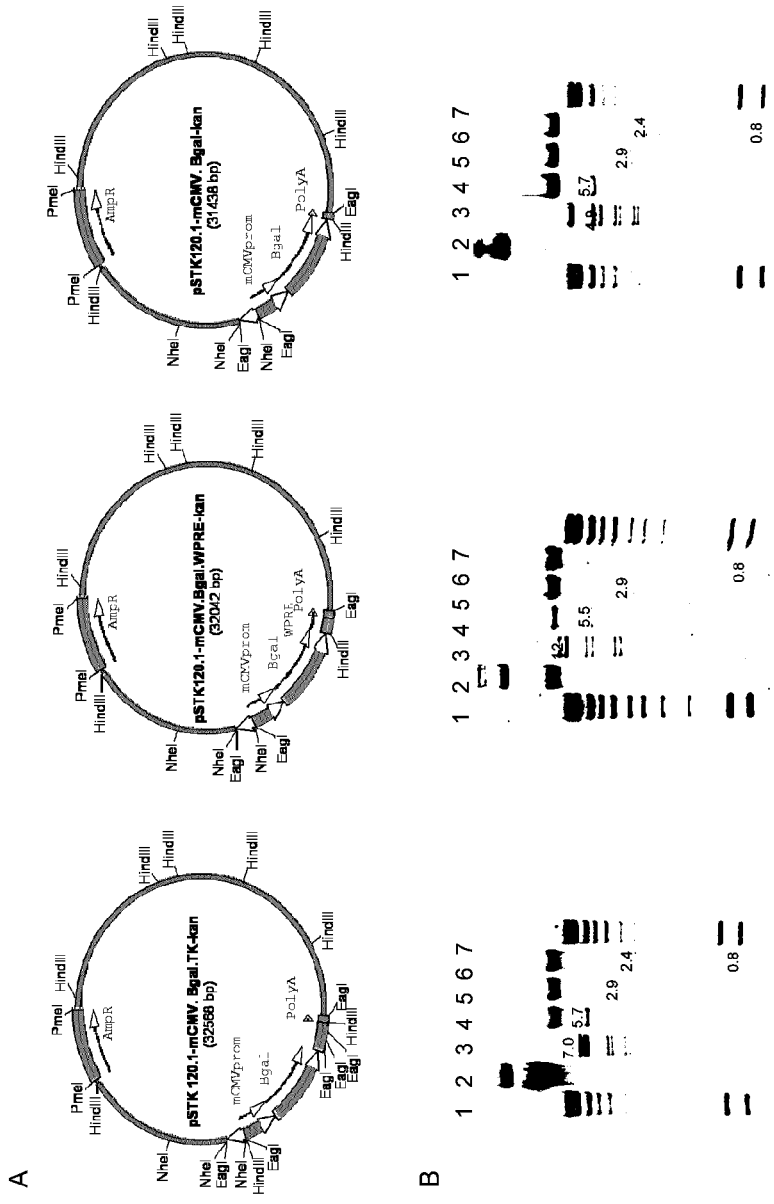
FIG. 2 depicts a schematic representation of pSTK120.1-mCMV.βgal.TK, approximately 32.566 kb (left panels); pSTK120.1-mCMV.βgal.WPRE, approximately 32.042 kb (center panels); and pSTK120-mCMV.βgal, approximately 34.401 kb (right panels) in accordance with various embodiments of the present invention. (A) HCAd plasmids maps indicate the constituents of the mCMV-driven βgal cassette within a pSTK gutless plasmid. (B) Gel electrophoresis and restriction map analysis of HCAd plasmid DNA to check for expected band sizes. For all gels the lanes are the same: Lanes 1 and 7, Hyperladder; lane 2, undigested DNA; lane 3, HindIII digest; lane 4, EagI digest; lane 5, PmeI digest; lane 6, NheI digest. (C) Linear depiction of the HCAd vector encoding the mCMV-driven βgal transgene. The constructs indicate the individual components and the orientation of the cassettes and their promoters. Some restriction enzymes are shown with the appropriate size fragments which correspond to the sizes indicated in panel B.
Figure 2:
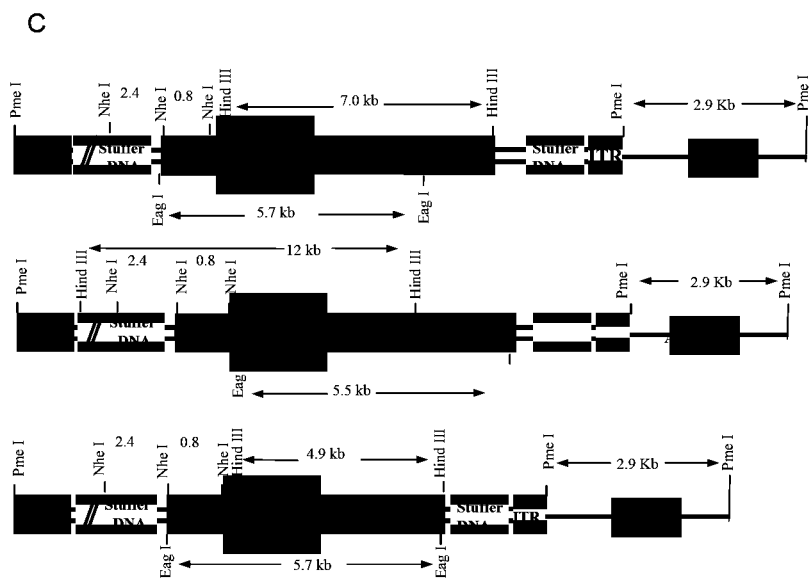

Herein the inventors describe the results of testing their belief that the HSV1-TK sequence fused to the 3' end of β-galactosidase increases transgene expression (shown schematically in FIG. 1). The inventors constructed first generation and HCAd vectors, utilizing the mCMV promoter to drive expression of β-galactosidase, the 1131 by of HSV1-TK was cloned downstream of β-galactosidase, and WPRE (594 bp) was used as a control post-transcriptional regulatory element (Appleby et al. (2003). A novel combination of promoter and enhancers increases transgene expression in vascular smooth muscle cells in vitro and coronary arteries in vivo after adenovirus-mediated gene transfer. Gene Ther 10:1616-22; Glover et al. (2002). Adenoviral-mediated, high-level, cell-specific transgene expression: a SYN1-WPRE cassette mediates increased transgene expression with no loss of neuron specificity. Mol Ther 5:509-16; Mian et al. (2004). Long-term correction of ornithine transcarbamylase deficiency by WPRE-mediated overexpression using a helper-dependent adenovirus. Mol Ther 10:492-9; Puntel et al. (2006). Quantification of high-capacity helper-dependent adenoviral vector genomes in vitro and in vivo, using quantitative TaqMan real-time polymerase chain reaction. Hum Gene Ther 17:531-44; Xu et al. (2003). Woodchuck hepatitis virus post-transcriptional regulation element enhances transgene expression from adenovirus vectors. Biochim Biophys Acta 1621:266-71). The plasmids used in the construction of HCAd-mCMV.βgal, HCAd-mCMV.βgal.TK, and HCAd-mCMV.βgal.WPRE are shown in FIG. 2; the same expression cassettes were also utilized in the production of Ad-mCMV.βgal, Ad-mCMV.βgal.TK, and Ad-mCMV.βgal.WPRE. All vectors were scaled up, titered and characterized for potency and quality control (LPS and RCA contamination) as described before (Dion et al. (1996). Supernatant rescue assay vs. polymerase chain reaction for detection of wild type adenovirus-contaminating recombinant adenovirus stocks. J Virol Methods 56:99-107; Puntel et al. (2006). Quantification of high-capacity helper-dependent adenoviral vector genomes in vitro and in vivo, using quantitative TaqMan real-time polymerase chain reaction. Hum Gene Ther 17:531-44; Southgate et al. (2000). Gene transfer into neural cells in vivo using adenoviral vectors, p. 4.23.1-4.23.40. In C. R. Gerfen, McKay, R., Rogawski, M. A., Sibley, D. R., Skolnick, P. (ed.), Current Protocols in Neuroscience, vol. 4.23.1-4.23.40. John Wiley and Sons, New York, N.Y., N.Y.). Vector preparations were titrated using BFU (β-galactosidase forming units) and vector-specific qPCR (Puntel et al. (2006). Quantification of high-capacity helper-dependent adenoviral vector genomes in vitro and in vivo, using quantitative TaqMan real-time polymerase chain reaction. Hum Gene Ther 17:531-44). The vectors obtained had the following titers: Ad-mCMV-βgal: $1.64 \times 10^{11}$ BFU/ml and $8.19 \times 10^{10}$ genomes/ml; Ad-mCMV.βgal.TK: $3.28 \times 10^{11}$ BFU/ml and $8.19 \times 10^{10}$ genomes/ml; Ad-mCMV.βgal.WPRE $5.12 \times 10^{9}$ BFU/ml and $2.56 \times 10^{9}$ genomes/ml; HCAd-mCMV.βgal $5.12 \times 10^{9}$ BFU/ml and $8.00 \times 10^{7}$ genomes/ml; HCAd-mCMV.βgal.TK $5.12 \times 10^{9}$ BFU/ml and $8.00 \times 10^{7}$ genomes/ml; HCAd-mCMV.βgal.WPRE $2.44 \times 10^{11}$ BFU/ml and $1.00 \times 10^{6}$ genomes/ml.

To determine the optimal, non-saturating, vector dose the inventors performed a dose-response curve, using the following cell lines: CNS1 (Lewis rats), GL26 (C57Bl/6 mice), J3T (dog), Cos 7 (primate), IN859 (human), U87 (human), and U251 (human) (data not shown); MOI 30 (based on BFU titers for all vectors, and well within the linear range of expression) was chosen for further analysis. Expression of β-galactosidase was tested in all cell lines, as described elsewhere (1, 3, 5, 36). β-galactosidase activity was determined using the following equation: enzymatic activity/min=[o-nitrophenol (mg/ml)]/(time (min)×[protein (mg/ml)]). Each assay was performed at least 2 times in triplicates, the results described herein correspond to the average value of one repetition representative of both experiments.

Figure 3:
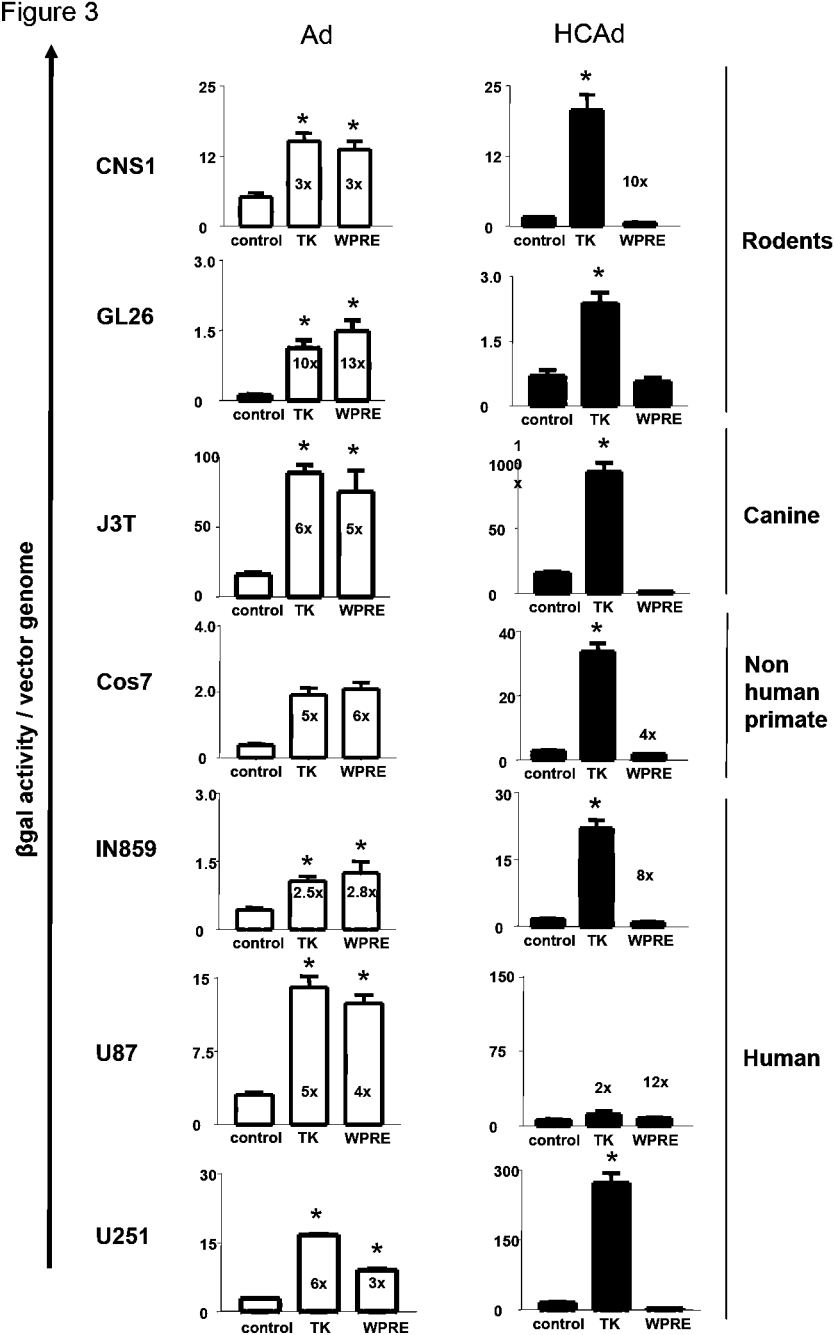
FIG. 3 depicts in vitro β-galactosidase activity per vector genome from first generation adenoviral vectors (Ad) (left panel) and High capacity Adenovirus vectors (HCAd) (right panel) from infected cell cultures in accordance with various embodiments of the present invention. Rat (CNS-1), mouse (GL26) and dog (J3T) glioma cells, monkey kidney cell line (Cos 7), one culture from a human glioma biopsy (IN859), and established human glioma cell lines (U87, U251) were infected with an MOI 30. Cells were incubated with the virus for 72 hours; transgene expression was determined by βgalactosidase activity assay on cell lysates. Genome copy numbers were determined for all the viral preparations using qPCR as described in the Materials and Methods section. Columns represent the means±SEM of βgalactosidase activity/vector genome calculated as [o-nitrophenol produced (mg/ml)/sample protein content (mg/ml)/incubation time (min)]/inoculated genomes. n=3 wells/group. Bonferroni analysis after One way ANOVA *, $P<0.05$ versus control group (infected cells with the corresponding vector bearing mCMV.βgal cassette). βgalactosidase activity/vector genome values are shown in arbitrary units where 1 is equivalent to 1×10⁶.
Figure 5:
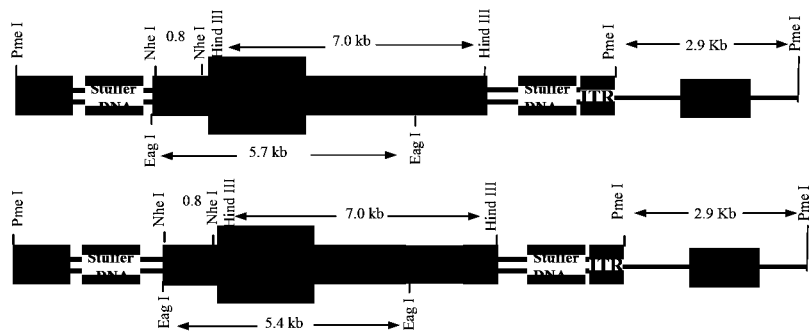
FIG. 5 depicts schematic representations of pSTK120 mCMV-βgalTK, approximately 32.566 kb (HC-Ad mCMV-βgalTK, left panels), and pSTK120 mCMV-βgalΔTK, approximately 32.514 kb (HC-Ad mCMV-βgalΔTK, right panels) in accordance with various embodiments of the present invention. (A) HC-Ad plasmids maps indicate the constituents of the mCMV-driven βgal cassette within a pSTK gutless plasmid. (B) Gel electrophoresis and restriction map analysis of HC-Ad plasmid DNA to check for expected band sizes. (C) Linear depiction of the HC-Ad vector encoding the mCMV-driven βgal transgene. The constructs indicate the individual components and the orientation of the cassettes and their promoters. Some restriction enzymes are shown with the appropriate size fragments which correspond to the sizes indicated in B.
Figure 6:
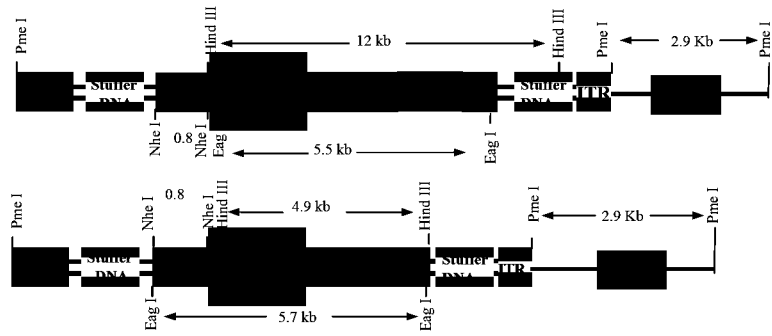
FIG. 6 depicts schematic representations of pSTK120 mCMV-βgal WPRE, approximately 32.042 kb (HC-Ad mCMV-βgal WPRE, left panels), and pSTK120 mCMV-βgal, approximately 34.401 kb (HC-Ad mCMV-βgal, right panels). (A) HC-Ad plasmids maps indicate the constituents of the mCMV-driven βgal cassette within a pSTK gutless plasmid. (B) Gel electrophoresis and restriction map analysis of HC-Ad plasmid DNA to check for expected band sizes. (C) Linear depiction of the HC-Ad vector encoding the mCMV-driven βgal transgene. The constructs indicate the individual components and the orientation of the cassettes and their promoters. Some restriction enzymes are shown with the appropriate size fragments which correspond to the sizes indicated in B.

The HSV1-TK sequence within first generation increased βgal activity per vector genome in all cell lines. The increase in expression/vector genomes ranged from 2.5- to 10-folds compared to the control vector (absence of HSV1-TK elements). Increased expression was comparable to that provided by WPRE (FIG. 3, left panels). The enhancement provided by WPRE was similar to results reported by others utilizing viral vectors; and the effects of HSV1-TK were analogous to previous data using transfection experiments (Appleby et al. (2003). A novel combination of promoter and enhancers increases transgene expression in vascular smooth muscle cells in vitro and coronary arteries in vivo after adenovirus-mediated gene transfer. Gene Ther 10:1616-22, Otero et al. (1998). Splicing-independent expression of the herpes simplex virus type 1 thymidine kinase gene is mediated by three cis-acting RNA subelements. J Virol 72:9889-96).

Further, HCAd-mCMV.βgal.TK also showed increased βgal activity per genome that ranged from 2- to 18-fold over the control. The effect of WPRE was not significant (FIG. 3, right panels). The inventors have previously shown that the mCMV promoter provides the highest expression levels, when compared to other viral, or cell type specific promoters. While not wishing to be bound by any particular theory, the failure of WPRE to increase expression significantly in these experiments may be due to the use of the strong mCMV promoter.

The inventors further tested the effects of the HSV1-TK sequence on transgene expression from the HCAd vectors in vivo. Adult female C57BL/6 mice of 18-25 grams body weight were used for in vivo HCAd mediated gene delivery. Four mice (n=4) were injected with a non-saturating dose of $5.0 \times 10^4$ BFU of vector (HCAd-mCMV.βgal or HCAd-mCMV.βgal.TK) into the striatum as described earlier (Southgate et al. (2000). Gene transfer into neural cells in vivo using adenoviral vectors, p. 4.23.1-4.23.40. In C. R. Gerfen, McKay, R., Rogawski, M. A., Sibley, D. R., Skolnick, P. (ed.), Current Protocols in Neuroscience, vol. 4.23.1-4.23.40. John Wiley and Sons, New York, N.Y., N.Y.; Xiong et al. (2006). Regulatable Gutless Adenovirus Vectors Sustain Inducible Transgene Expression in the Brain in the Presence of an Immune Response against Adenoviruses. J Virol 80:27-37).

Seven days post-injection animals were perfused with approximately 100 ml oxygenated Tyrode's solution followed by a 4% paraformaldehyde solution. Brains were serially sectioned using an electronic vibratome (Leica) to obtain 50 μm free floating sections. Sections were then immunoreacted using rabbit polyclonal anti-β-galactosidase primary antibody (1:1000) [generated in the inventors' laboratory (Ali et al. (2005). Combined immunostimulation and conditional cytotoxic gene therapy provide long-term survival in a large glioma model. Cancer Res 65:7194-204; Smith-Arica et al. (2001). Switching on and off transgene expression within lactotrophic cells in the anterior pituitary gland in vivo. Endocrinology 142:2521-32, Southgate et al. (2001). Long-term transgene expression within the anterior pituitary gland in situ: impact on circulating hormone levels, cellular and antibody-mediated immune responses. Endocrinology 142:464-76; Thomas et al. (2001). Preexisting antiadenoviral immunity is not a barrier to efficient and stable transduction of the brain, mediated by novel high-capacity adenovirus vectors. Hum Gene Ther 12:839-46)]. Brain sections containing the needle track (area of highest levels of immunoreactivity) were used for quantitative analysis. Bonferroni post-analysis after a one-way ANOVA test was used to determine the degree of statistical significance between vectors βgal activity values in each cell line. Results were expressed as the number of β-galactosidase expressing cells per vector genome. The inventors found a 25.8-fold increase of βgal expressing cells per number of vector genomes in the brains of mice stereotactically injected with HCAd-mCMV.βgal.TK into the striatum, compared to the control vector HCAd-mCMV.βgal (FIG. 4). Taken together, the in vitro and in vivo results demonstrate that the HSV1-TK sequence increases levels of transgene expression per vector genome.

Immune responses to viral vectors constitute one of the limitations of gene therapy. Recent improvements to vectors that take immunological challenges into consideration have facilitated the use of viral vectors in clinical trials (Gahery-Segard et al. (1997). Phase I trial of recombinant adenovirus gene transfer in lung cancer. Longitudinal study of the immune responses to transgene and viral products. J Clin Invest 100:2218-26; Molinier-Frenkel et al. (2000). Immune response to recombinant adenovirus in humans: capsid components from viral input are targets for vector-specific cytotoxic T lymphocytes. J Virol 74:7678-82). Additional increases in transgene expression per vector genome would allow furthering reducing viral vector doses needed. WPRE has been systematically evaluated as a post-transcriptional regulatory element to increase transgene expression in adenoviral (Appleby et al. (2003). A novel combination of promoter and enhancers increases transgene expression in vascular smooth muscle cells in vitro and coronary arteries in vivo after adenovirus-mediated gene transfer. Gene Ther 10:1616-22; Boulos et al. (2006). Assessment of CMV, RSV and SYN1 promoters and the woodchuck post-transcriptional regulatory element in adenovirus vectors for transgene expression in cortical neuronal cultures. Brain Res 1102:27-38; Mian et al. (2004). Long-term correction of ornithine transcarbamylase deficiency by WPRE-mediated overexpression using a helper-dependent adenovirus. Mol Ther 10:492-9; Xu et al. (2003). Woodchuck hepatitis virus post-transcriptional regulation element enhances transgene expression from adenovirus vectors. Biochim Biophys Acta 1621:266-71), retroviral (Hlavaty et al. (2005). Effect of post-transcriptional regulatory elements on transgene expression and virus production in the context of retrovirus vectors. Virology 341:1-11; Klein et al. (2006). WPRE-mediated enhancement of gene expression is promoter and cell line specific. Gene 372:153-61), lentiviral (Dupuy et al. (2005). Lentiviral transduction of human hematopoietic cells by HIV-1- and SIV-based vectors containing a bicistronic cassette driven by various internal promoters. J Gene Med 7:1158-71; Mautino et al. (2002). Enhanced inhibition of human immunodeficiency virus type 1 replication by novel lentiviral vectors expressing human immunodeficiency virus type 1 envelope antisense RNA. Hum Gene Ther 13:1027-37; Moreau-Gaudry et al. (2001). High-level erythroid-specific gene expression in primary human and murine hematopoietic cells with self-inactivating lentiviral vectors. Blood 98:2664-72; Ramezani et al. (2000). Lentiviral vectors for enhanced gene expression in human hematopoietic cells. Mol Ther 2:458-69), and AAV vectors (Loeb et al. (1999). Enhanced expression of transgenes from adeno-associated virus vectors with the woodchuck hepatitis virus posttranscriptional regulatory element: implications for gene therapy. Hum Gene Ther 10:2295-305; Martin et al. (2003). Gene therapy with brain-derived neurotrophic factor as a protection: retinal ganglion cells in a rat glaucoma model. Invest Opthalmol Vis Sci 44:4357-65; Peden et al. (2004). Circulating anti-wild-type adeno-associated virus type 2 (AAV2) antibodies inhibit recombinant AAV2 (rAAV2)-mediated, but not rAAV5-mediated, gene transfer in the brain. J Virol 78:6344-59, Virella-Lowell et al. (2005). Enhancing rAAV vector expression in the lung. J Gene Med 7:842-50); though its use in HSV1-derived vectors has not been described. In these various vector systems WPRE increased transgene expression when tested with constitutive promoters such as the hCMV promoter or cell type-specific promoters. In various models and vectors WPRE increased expression by 3-10 times, similar to the increased expression observed in our experiments.

Thus, highest levels of transgene expression were achieved through the combined use of the mCMV promoter and HSV1-TK encoded within HCAd, both in vitro (especially in human cell lines) and in vivo. This combination is particularly significant in that so far, the mCMV promoter represents the strongest promoter within adenoviral vectors. To the best of the inventors' knowledge, the combination of the mCMV promoter and the HSV1-TK element constitutes the strongest transcriptional expression cassette. The fact that highest expression levels per vector genome was obtained following infection of human cells, supports the use of these vectors for the treatment of brain disorders, especially brain gliomas (all human cell lines analyzed are human glioma-derived). In summary, herein the inventors demonstrate the increase in transgene expression provided by HSV1-TK acting as a post-transcriptional regulatory element within adenoviral vectors.

One skilled in the art will recognize many methods and materials similar or equivalent to those described herein, which could be used in the practice of the present invention. Indeed, the present invention is in no way limited to the methods and materials described. For purposes of the present invention, the following terms are defined below.

EXAMPLES

The following examples are provided to better illustrate the claimed invention and are not to be interpreted as limiting the scope of the invention. To the extent that specific materials are mentioned, it is merely for purposes of illustration and is not intended to limit the invention. One skilled in the art may develop equivalent means or reactants without the exercise of inventive capacity and without departing from the scope of the invention.

Example 1

Engineering of the Transgene and Postranscriptional Elements pBluescript II SK(+) (Stratagene, La Jolla, Calif.) was modified as described previously (Candolfi, 2006) originating pBS-MCS1 with Multiple Cloning Site 1 (MCS1) containing NotI, AscI, NheI and HindIII; in order to clone the cassettes bearing HSV-1 TK generating pBS-MCS8 with a MCS containing KpnI, NotI, AvrII, HindIII, NheI, NotI, SacI. In both pBSMCS1 and pBSMCS8 vectors Kanamycin was cloned into NheI site, and a cassette containing mCMV promoter and SV40 polyA was cloned into HindIII. The cassettes containing the transgene and post-transcriptional elements were cloned into SalI site of the corresponding vector. A third modification of the pBluescript II SK(+) with a MCS6 containing SalI, BamHI, EcoRI, XbaI, PvuII, BglIISalI, ClaI, HindIII, generated the pBSMCS6.

The βgalactosidase cassette (βgal) transgene was excised by BamHI digestion from PAL119 βgal (RAd 35), and cloned into pBSMCS6, generating pBMCS6βgal (6093 bp). Thymidine kinase was excised from PAL119 TK with BamHI and cloned into βglII of the pBSMCS6βgal vector, generating pBSMCS6βgal-TK (7238 bp). Internal ribosome responsive element (IRES) from pIRES 6.1 kb (Clontech) was cloned in the EcoRI site of pBSMCS6βgal-TK (8047 bp). A cassette bearing mCMV-βgal-WPRE (Woodchuck virus post-transcriptional element) was excised from pΔppLacZ vector 12.3 kb (Umania) with HindIII and BamHI, and was cloned into HindIII/BglII of pBSMCS1-kan, generating pBMCS1-mCMV-βgal-WPRE-kan (6599 bp).

For generating a 60 bp deletion in HSV1TK, PCR was performed using the following primers: TK1, forward primer, 5' TCCTTCAGATCTTCAGTTAGC 3' (SEQ ID NO. 2) (that hybridizes at base pair 60 downstream the start codon for the TK gene), and TK2 reverse primer, 5'CGTTCTAGATCT-CATAACAAC 3' (SEQ ID NO.3). The ΔTK insert was cloned first in pGemTEasy generating the pGemTEasyΔTK vector (4105 bp), excised with βglII and cloned into the βglII of the pBMCS6βgal vector, generating the pMCS6βgal-ΔTK (7993 kb).

Subsequently, all the cassettes contained into the pBSMCS6 vectors were excised from the vector by SalI digestion and cloned into the SalI site of pBSMCS8-kan vector generating pBSMCS8-mCMV-βgal-Kan, pBSMCS8-mCMV-βgal-TK-Kan, pBSMCS8-mCMV-βgal-ΔTK-Kan, pBSMCS8-mCMV-βgal-IRES-TK-Kan.

Example 2

Engineering of HC-Ad Plasmids

The insert mCMV βgal-kan was excised with NotI cloned into the EagI pSTK120, generating pSTK120mCMV-βgal, generation of the pSTK120 hCMV-βgal vector has been described previously (Umana et al. (2001). Efficient FLPe recombinase enagles scalable production of helper-dependent adenoviral vectors with negligible helper-virus contamination. Nature Biotechnology. 19(6):582-5). The inserts mCMV-βgal-kan, mCMV-βgal-ΔTK-kan, mCMV-βgal-WPRE-kan and mCMV-βgal-IRES-TK-kan, were excised with AvrII and cloned into the compatible NheI site of pSTK120.1 previously described (Wei), generating pSTK120.1 mCMV-βgal-TK, pSTK120.1 mCMV-βgal-ΔTK, pSTK120.1 mCMV-βgal-WPRE, and pSTK120.1 mCMV-βgal-IRES-TK.

Example 3

Production, Scale Up and Purification of HC-Ad Vectors

HC-Ad vectors were generated using 10 µg of HC-Ad plasmid DNA that was linearized using Pme I, heat inactivated, and transfected into 293FLPe cells using the calcium phosphate method. Transfected 293 cells were co-infected with FL helper virus (Umana et al. (2001). Efficient FLPe recombinase enagles scalable production of helper-dependent adenoviral vectors with negligible helper-virus contamination. Nature Biotechnology. 19(6):582-5) (previously generated in the inventors' laboratory) with a multiplicity of infection (M.O.I.) of 5 (passage 0). All subsequent infections in the amplification were done using an M.O.I. of 1. After full cytopathic effect (CPE) was observed for each passage, 1.5× $10^6$ of pre-seeded confluent 293FLPe cells were adsorbed for one hour with 0.5 ml of the cell lysate from the preceding passage (after three cycles of freeze/thaw for membrane lysis and viral release), followed by infection with FL helper virus with an M.O.I. of 1. Cells were incubated at 37° C. for 2-3 days until full CPE was observed. Subsequent passages were performed in the same manner with identical corresponding M.O.I. infections until passage 7 was reached. Subsequent scale up, purification, and end point titrations of HC-Ad vectors were done as previously described (Umana et al. (2001). Efficient FLPe recombinase enagles scalable production of helper-dependent adenoviral vectors with negligible helper-virus contamination. Nature Biotechnology. 19(6):582-5; Lowenstein et al. (2002). Progress and challenges in viral vector-mediated gene transfer to the brain. Current Opinions in Molecular Therapy. 4(4): 359-371; Lowenstein et al. (2002). High-capacity, helper-dependent, "gutless" adenoviral vectors for gene transfer into brain. Methods Enzymol. 346:292-311). Large titers of HC-Ad vectors, which were used to assess regulated and persistent gene expression in preimmunized animals, were scaled up and purified using the 293Cre cell system as previously described (Palmer et al. (2003). Improved system for helper-dependent adenoviral vector production. Mol Ther. 8(5):846-52; Palmer et al. (2004). Physical and infectious titers of helper-dependent adenoviral vectors: a method of direct comparison to the adenovirus reference material. Mol Ther. 10(4): 792-8).

Example 4

Engineering, Rescue and Purification of First Generation Ad Vectors

The inserts mCMV-βgal-TK-kan, mCMV-βgal-ΔTK-kan, and mCMV-βgal-WPRE-kan described herein were excised with NotI cloned into the NotI site of pΔE1sp1A, generating pΔE1sp1A-mCMV-βgal-TK, pΔE1sp1A-mCMV-βgal-ΔTK-kan, and pΔE1sp1A-mCMV-βgal-WPRE-kan. The corresponding vectors, i.e., Ad-mCMV-βgal-TK, mCMV-βgal-ΔTK and Ad-mCMV-βgal-WPRE, were rescued by cotransfection of 293 cells with pJM17, plaque purified, and scaled up by infecting human embryonic kidney HEK 293 cells with a multiplicity of infection (MOI) of 3 infectious units (IU)/cell of vector seed stock. Vectors were titered in triplicate by end-point dilution, cytopathic effect assay (Southgate et al. (2000). Gene transfer into neural cells in vivo using adenoviral vectors, p. 4.23.1-4.23.40. In C. R. Gerfen, McKay, R., Rogawski, M. A., Sibley, D. R., Skolnick, P. (ed.), Current Protocols in Neuroscience, vol. 4.23.1-4.23.40. John Wiley and Sons, New York, N.Y., N.Y.).

Example 5

Vector Characterization

Viral vector particles per milliliter were measured at OD260 with a spectrophotometer (Beckman Coulter, Fullerton, Calif., USA), and blue forming units (BFU). For high capacity vectors, helper virus was titered using pfu/ml. LPS contamination (Cambrex, East Rutherford, N.J., USA) and replication-competent adenovirus were detected using a biological assay for all the vector preparations. Vector genomes quantification was performed by Real time PCR (qPCR).

Example 6

In Vitro HC-Ad or Ad Infection and β-Galactosidase Activity

Expression of β-galactosidase from HCAd and Ad vectors was tested in CNS-1 (rat), GL26 (balb/c mice), IN859 (human), J3T (dog), glioma cell lines, or U251 and U87 human glioma primary cultures, or Cos 7 (monkey) kidney fibroblast cell line. Twenty-four hours prior to HC-Ad virus infection, cells were plated in 24-well plates at a density of $75 \times 10^3$ cells/well in DMEM medium containing 10 μl/ml non essential aminoacids, 10 μl/ml L-glutamine, 10 μl/ml penicillin-streptomycin and 10% fetal calf serum (Invitrogen). Cells were infected with MOIs 1, 3, 30, and 100 of each vector, i.e., first generation vectors Ad-βgal and Ad-βgal.TK, Ad-βgal.ΔTK, and Ad-βgal.WPRE, and high capacity vectors: HCAd-βgal, HC-Ad-βgal.TK, HC-Ad-βgal.ΔTK, HCAd-βgal.WPRE, and HC-Ad-βgal.IRES.TK; and were incubated for 72 hours. After incubation, cells were subjected to a single gentle wash with PBS, then gently scraped, centrifuged, and re-suspended in a volume of 30 μl of PBS containing 1× Halt Protease inhibitor cocktail EDTA-Free (Pierce) and the samples were stored at −70° C. until use. Cell suspensions were flash frozen and thawed three times and cellular debris were removed by centrifugation. The supernatants, containing protein extracts were transferred into fresh tubes. β-galactosidase assays were performed to measure the enzymatic activity of the transgene by means of color detection. β-galactosidase activity was measured by conversion of o-nitrophenyl-β-D-galactopyranoside in 10 mM MgCl2/0.45 M/2-mercaptoethanol. All samples were incubated at 37° C. and the enzymatic reaction was stopped with 510 μl 1M $Na_2CO_3$ (Ali et al. (2004). Inflammatory and anti-glioma effects of an adenovirus expressing human soluble Fms-like tyrosine kinase 3 ligand (hsFlt3L): treatment with hsFlt3L inhibits intracranial glioma progression. Mol Ther 10:1071-84). β-galactosidase activity measurements were recorded at 420 nm absorbance from a nitrophenol standard curve using o-nitrophenol substrate. Protein sample measurements were determined at 562 nm absorbance from a standard protein curve produced using BCA protein assay reagent (Promega, U.S.A.). The β-galactosidase activity was determined using the mathematical equation: enzymatic activity/min=[o-nitrophenol (mg/ml)]/(time (min)×[protein (mg/ml)]).

Example 7

Stereotactic Neurosurgery

Adult female C57BL/6 mice of 18-25 g body weight were used for in vivo HCAd mediated gene delivery. Four mice (n=4) were injected with each vector HCAd-βgal and HCAd-βgal.TK in the striatum (coordinates from bregma: anterior: 0.5 mm; lateral: 2.2 mm; ventral: 3.0 mm), using a 10 μl Hamilton syringe (Smith-Arica et al. 2000. Cell-type-specific and regulatable transgenesis in the adult brain: adenovirus-encoded combined transcriptional targeting and inducible transgene expression. Mol Ther. 2(6): 579-87). A total volume of 1 μl of HCAd vector diluted in 0.9% w/v saline was injected in the striatum per animal over a 3 min period. Subsequent to vector injection, the needle was left in place for a further 2 min prior to careful needle retraction. Control mice received 1 μl saline injections. After seven days post-injection, both untreated and treated animals were sacrificed and brains perfused with approximately 100 ml oxygenated Tyrode's solution (0.14 M NaCl, 1.8 mM $CaCl_2$, 2.7 mM KCl, 0.32 mM $NaH_2PO_4$, 5.6 mM glucose and 11.6 mM $NaHCO_3$) by means of trans-cardial perfusion and 4% paraformaldehyde fixation. Brains were serial sectioned using an electronic VT1000S vibrating blade vibratome (Leica) to obtain 50 μm free floating sections. Sections were stored in PBS containing 0.1% sodium azide at 4° C. until ready for use.

Example 8

Immunohistochemistry

Free floating brain sections were washed with TBS and 0.5% Triton followed by 0.3% $H_2O_2$ incubation to inactivate endogenous peroxidase. Non-specific antibody sites and Fc receptors were blocked with 10% normal horse serum for one hour. Sections were incubated for forty-eight hours at room temperature with rabbit polyclonal anti-β-galactosidase primary antibody (1:1000) [generated in the inventors' laboratory, (Thomas et al. (2000). peripheral infection with adenovirus causes unexpected long-term brain inflammation in animals injected intracranially with first-generation, but not with high-capacity, adenovirus vectors: Toward realistic long-term neurological gene therapy for chronic diseases. PNAS. 97(13):7482-87; Smith-Arica et al. (2001). Switching on and off transgene expression within lactotrophic cells in the anterior pituitary gland in vivo. Endocrinology 142:2521-32; Southgate et al. (2001). Long-term transgene expression within the anterior pituitary gland in situ: impact on circulating hormone levels, cellular and antibody-mediated immune responses. Endocrinology 142:464-76; Ali et al. (2005). Combined immunostimulation and conditional cytotoxic gene therapy provide long-term survival in a large glioma model. Cancer Res 65:7194-204)] diluted in TBS/0.5% Triton/1% horse serum/0.1% sodium azide. Sections were washed 3 times with TBS+0.5% Triton and then incubated with goat anti-rabbit biotinylated secondary antibody (1:800) (Dako, USA) for four hours. The avidin/biotinylated HRP complex was prepared and used for detection using Vectastain ABC Elite kit (Vector laboratories, USA). Following staining with diaminobenzidine (DAB) and glucose oxidase, sections were mounted on gelatin coated glass slides, dehydrated through graded ethanol solutions, and carefully covered for microscopy.

Example 9

Quantitative Stereological Analysis

Quantitative analysis to determine the anatomical area occupied by cells immunoreactive with antibodies against β-galactosidase and immune markers in 50 µm brain sections was performed using a Zeiss AxioPlan 2 Imaging microscope (Carl Zeiss Microsystems, Inc., Thornwood, N.Y., USA) controlled by a Ludl electronic MAC 5000 XY stage control (Ludl Electronics Products Ltd, Hawthorne, N.Y., USA). Brain sections containing the needle track (area of highest levels of immunoreactivity) were used for quantitative analysis. Boferroni post-analysis after a One way ANOVA test was used to determine the degree of statistical significance between vectors βgal activity values in each cell line (Suwelack et al. (2004). Neuronal expression of the transcription factor Gli 1 using the T alpha 1 alpha-tubulin promoter is neuroprotective in an experimental model of Parkinson's disease. Gene Therapy. 11(24): 1742-52).

Example 10

Generation and Characterization of βgal-Expressing First Generation Adenoviral Vectors (Ad) with Different Post-Transcriptional Regulatory Sequences The inventors have previously demonstrated that a strong promoter is necessary to achieve high levels of transgene expression allowing to reduce the vector dose and thus, eliminate inflammatory side effects (Gerdes et al. (2000). Strong promoters are the key to highly efficient, noninflammatory and noncytotoxic adenoviral-mediated transgene delivery into the brain in vivo. Mol Ther. 2(4):330-8). The inventors, therefore, chose the murine major immediate early cytomegalovirus (mCMV) driving the expression of βgal and cloned two different cassettes with TK as a posttranscriptional regulatory signal, using the complete TK ORF in Ad-βgal.TK; or using a 60 bp deleted TK sequence in Ad-βgal.ΔTK; the inventors used Woodchuck Hepatitis virus Postranscriptional Regulatory Element as a control in Ad βgal.WPRE. After confirming the presence and the required orientation of the cassette and the βgal expression of the cassettes, the inventors proceeded to construct, scale up and purify both Ad and HCAd vectors as previously described (Southgate et al., 2000. Gene transfer into neural cells in vivo using adenoviral vectors, p. 4.23.1-4.23.40. In C. R. Gerfen, McKay, R., Rogawski, M. A., Sibley, D. R., Skolnick, P. (ed.), Current Protocols in Neuroscience, vol. 4.23.1-4.23.40. John Wiley and Sons, New York, N.Y., N.Y.; Umana et al. (2001). Efficient FLPe recombinase enagles scalable production of helper-dependent adenoviral vectors with negligible helper-virus contamination. Nature Biotechnology. 19(6): 582-5; Lowenstein et al. (2002). High-capacity, helper-dependent, "gutless" adenoviral vectors for gene transfer into brain. Methods Enzymol. 246: 292-311; Palmer et al. (2004). Physical and infectious titers of helper-dependent adenoviral vectors: a method of direct comparison to the adenovirus reference material. Mol Ther. 10(4):792-8; Palmer et al. (2005). Helper-dependent adenoviral vectors for gene therapy. Hum Gene Ther. 16(1): 1-16).

All Ad and HCAd vector preparations were titrated using IU (infectious viral particles, plaque forming units), BFU (β-galactosidase forming units), OD260 (total viral particles), and vector-specific qPCR (Puntel et al. (2006). Quantification of high-capacity helper-dependent adenoviral vector genomes in vitro and in vivo, using quantitative TaqMan real-time polymerase chain reaction. Hum Gene Ther 17:531-44). Each vector preparation was evaluated for the presence of bacterial lipopolysaccharide (LPS) and replication competent Ad (RCA), as described before (Dion et al. (1996). Supernatant rescue assay vs. polymerase chain reaction for detection of wild type adenovirus-contaminating recombinant adenovirus stocks. J Virol Methods 56:99-107; Southgate et al. (2000). Gene transfer into neural cells in vivo using adenoviral vectors, p. 4.23.1-4.23.40. In C. R. Gerfen, McKay, R., Rogawski, M. A., Sibley, D. R., Skolnick, P. (ed.), Current Protocols in Neuroscience, vol. 4.23.1-4.23.40. John Wiley and Sons, New York, N.Y., N.Y.). All the Ad and HCAd vectors tested negative for LPS and RCA contamination (Table 1).

In order to determine the optimal virus dose for all the vectors that shown the maximal transgene expression in vitro (data not shown), the inventors performed a dose curve using four multiplicity of infection (MOI) 1, 3, 30, 100. Since the inventors wanted to know if the effects of TK were species-specific, they decided to perform the dose response study in all the cell cultures that were studied: CNS1, GL26, J3T, IN859, U87, U251 and Cos 7 (data not shown), from the results the inventors picked MOI 30 for further analysis.

Example 11

TK Sequences Affect Positively Transgene Expression in Ad and HCAd Vectors In Vitro The inventors analyzed the influence of TK sequences on the βgal expression in the context of the adenoviral genome, i.e., first generation adenovirus-derived vectors (Ad). To do so, the inventors analyzed in vitro the βgal activity per inoculated vector genome. The results showed a clear tendency of increased βgal activity per vector genome under the presence of TK sequences in the construct that was consistent for all the cell cultures analyzed and that ranged between 2.5- to 10-folds compared to the control (mCMV.βgal cassette). These levels were equivalent to those detected with WPRE as a posttranscriptional regulatory sequence. The results showed a clear increase in the levels of transgene expression specifically under the presence of TK sequences in the construct. On the contrary, the vector bearing a 60 bp deletion of TK did not show any influence on the βgal activity.

To investigate whether the backbone makes a difference in the effect of these regulatory sequences on the levels of transgene expression, the inventors studied the effect of the TK sequences on the transgene expression when the background is a HCAd. That is, in the absence of Adenoviral genomic sequences, the inventors cloned the same cassettes described before in a modified pSTK120 vector (described in detail in (Xiong et al. (2006). Regulatable Gutless Adenovirus Vectors Sustain Inducible Transgene Expression in the Brain in the Presence of an Immune Response against Adenoviruses. J Virol 80:27-37)) and constructed two different HCAd vectors with TK as a posttranscriptional regulatory signal, HCAd-βgal.TK; HCAd-βgal.ΔTK; and the control HCAd-βgal.WPRE; and in order to know if the expression of TK would be needed for the up-regulation of the transgene expression, the inventors added an Internal Ribosome Responsive Element (IRES) downstream the βgal gene and upstream the TK gene.

Between the high capacity vectors, HCAd-βgal.TK, HCAd-βgal.ΔTK and HCAd-βgal.IRES.TK were the vectors that showed increased βgal activity per genome. HCAd-βgal.IRES.TK showed a maximum of 7-fold βgal activity increase compared to the control HCAd-βgal, while HCAd-βgal.TK showed increases that ranged from 2- to 18-fold over the control, and HCAd-βgal.ΔTK showed increases that ranged from 4- to 26-fold over the control in the different cell lines. The effect of WPRE on the expression of the transgene was not noticeable.

Example 12

TK Sequences Increase Transgene Expression In Vivo

The inventors further found a 25.8-fold increase of βgal expressing cell in the brains of mice stereotactically injected with HCAd-βgal.TK, compared to the control vector HCAd-βgal (dose $5.0 \times 10^4$ BFU).

Example 13

Enhancers

Woodchuck hepatitis virus post-transcriptional regulatory element (WPRE) has been systematically evaluated post-transcriptional regulatory elements in the context of adenovirus derived vectors, both in first generation vectors or high capacity, retroviral vectors and in transfected cell lines. Another sequence described to act in cis regulating the expression of upstream transgenes is HSV1 Thymidine kinase. A 119 by sequence that binds proteins such as hnRNP L and enables cytoplasmic accumulation of the mRNA encoded. As well, Otero and Hope (1995) showed that TK acts enhancing the cytoplasmic RNA accumulation, and shares some features with WPRE (Otero, 1995). Furthermore, in the same HVS1 infection cycle TK has a role on the expression of neighboring genes (Cook et al. (1986). Expression of the adenovirus E1A oncogene during cell transformation is sufficient to induce susceptibility to lysis by host inflammatory and noncytotoxic adenoviral-mediated transgene delivery into the brain in vivo. Mol Ther. 2(4):330-8). The inventors compared the effect of TK sequences on transgene expression levels for both first generation and high capacity Ad-derived vectors in brain tissue from different species. The results showed that the transgene expression enhancement that TK exerts is a more universal effect that occurs independently of the vector backbone compared to the effect of WPRE that apparently requires in some way the presence of the viral genome for it to happen.

While the description above refers to particular embodiments of the present invention, it should be readily apparent to people of ordinary skill in the art that a number of modifications may be made without departing from the spirit thereof. The presently disclosed embodiments are, therefore, to be considered in all respects as illustrative and not restrictive.

What is claimed:

1. A high capacity adenoviral expression vector capable of enhancing the expression of a transgene, comprising:
   a polynucleotide consisting of base pairs 196 through 1131 of SEQ ID NO: 1; and
   the transgene,
   wherein the polynucleotide is fused to the 3' end of the transgene and is not translated into an amino acid sequence.

2. The expression vector of claim 1, further comprising an mCMV promoter.

3. The expression vector of claim 2, wherein the mCMV promoter is operably linked to the transgene and the polynucleotide.

4. A method of enhancing the expression of a transgene, comprising:
   providing a high capacity adenoviral expression vector comprising: a polynucleotide consisting of base pairs 196 through 1131 of SEQ ID NO: 1; and the transgene;
   introducing the expression vector into a cell; and
   maintaining the cell under conditions permitting increased expression of the transgene,
   wherein the polynucleotide is fused to the 3' end of the transgene and is not translated into an amino acid sequence.

5. The method of enhancing the expression of a transgene of claim 4, wherein the cell is maintained in vivo.

6. The method of enhancing the expression of a transgene of claim 4, wherein the cell is maintained in vitro.

7. The method of enhancing the expression of a transgene of claim 4, wherein the expression vector further comprises an mCMV promoter.

8. The method of enhancing the expression of a transgene of claim 7, wherein the mCMV promoter is operably linked to the polynucleotide and the transgene.

9. A pharmaceutical preparation, comprising:
   a high capacity adenoviral expression vector capable of enhancing the expression of a transgene, comprising:
   a polynucleotide consisting of base pairs 196 through 1131 of SEQ ID NO: 1; and the transgene; and
   a pharmaceutically acceptable carrier,
   wherein the polynucleotide is fused to the 3' end of the transgene and is not translated into an amino acid sequence.

10. The pharmaceutical preparation of claim 9, wherein the expression vector further comprises an mCMV promoter.

11. The pharmaceutical preparation of claim 10, wherein the mCMV promoter is operably linked to the polynucleotide and the transgene.

12. A kit for enhanced expression of a transgene, comprising:
    a high capacity adenoviral expression vector, comprising: a polynucleotide consisting of base pairs 196 through 1131 of SEQ ID NO: 1; and the transgene;
    a pharmaceutically acceptable carrier; and
    instructions for use,
    wherein the polynucleotide is fused to the 3' end of the transgene and is not translated into an amino acid sequence.

13. The kit for enhanced expression of a transgene of claim 12, wherein the expression vector further comprises an mCMV promoter.

14. The kit for enhanced expression of a transgene of claim 13, wherein the mCMV promoter is operably linked to the polynucleotide and the transgene.

15. The kit for enhanced expression of a transgene of claim 12, wherein the kit is configured for in vivo expression of the transgene.

16. The kit for enhanced expression of a transgene of claim 12, wherein the kit is configured for in vitro expression of the transgene.

* * * * *